US006733967B1

(12) United States Patent
Kornman et al.

(10) Patent No.: US 6,733,967 B1
(45) Date of Patent: May 11, 2004

(54) FETAL TESTING FOR PREDICTION OF LOW BIRTH WEIGHT

(75) Inventors: Kenneth S. Kornman, Newton, MA (US); Gordon W. Duff, South Yorkshire (GB); Steven Offenbacher, Chapel Hill, NC (US)

(73) Assignees: Interleukin Genetics, Inc., Waltham, MA (US); The University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 09/693,555

(22) Filed: Oct. 20, 2000

Related U.S. Application Data

(63) Continuation-in-part of application No. PCT/US99/08794, filed on Apr. 21, 1999.
(60) Provisional application No. 60/082,487, filed on Apr. 21, 1998.

(51) Int. Cl.$^7$ .......................... C12Q 1/68; C12P 19/34; C07H 21/04
(52) U.S. Cl. ......................... 435/6; 435/91.2; 536/23.5; 536/24.31; 536/24.33
(58) Field of Search .................. 435/6, 91.2; 536/23.1, 536/23.5, 24.31, 24.33

(56) References Cited

U.S. PATENT DOCUMENTS

| | | | |
|---|---|---|---|
| 4,582,788 A | 4/1986 | Elrich | 435/6 |
| 4,656,127 A | 4/1987 | Mundy | 435/6 |
| 4,666,828 A | 5/1987 | Gusella | 435/6 |
| 4,683,195 A | 7/1987 | Mullis et al. | 435/6 |
| 4,683,202 A | 7/1987 | Mullis | 435/91 |
| 4,801,531 A | 1/1989 | Frossard | 435/6 |
| 4,833,080 A | 5/1989 | Brent et al. | 435/172.3 |
| 4,968,607 A | 11/1990 | Dower et al. | 435/69.1 |
| 4,998,617 A | 3/1991 | Ladd, Jr. et al. | 206/219 |
| 5,110,920 A | 5/1992 | Erlich | 536/27 |
| 5,153,117 A | 10/1992 | Simons | 435/2 |
| 5,192,659 A | 3/1993 | Simons | 435/6 |
| 5,268,267 A | 12/1993 | Smith | 435/6 |
| 5,272,057 A | 12/1993 | Smulson et al. | 435/6 |
| 5,457,024 A | 10/1995 | Goldbard | 435/2 |
| 5,593,826 A | 1/1997 | Fung et al. | 435/6 |
| 5,629,147 A | 5/1997 | Asgari et al. | 435/5 |
| 5,686,246 A | 11/1997 | Kornman et al. | 435/6 |
| 5,698,399 A | 12/1997 | Duff et al. | 435/6 |
| 6,268,142 B1 * | 7/2001 | Duff et al. | |

FOREIGN PATENT DOCUMENTS

| | | |
|---|---|---|
| WO | WO 91/02087 | 2/1991 |
| WO | WO 91/16452 | 10/1991 |
| WO | WO 92/15694 | 9/1992 |
| WO | WO 94/16101 | 7/1994 |
| WO | WO 97/06180 | 2/1997 |
| WO | WO 97/38135 | 10/1997 |
| WO | WO 98/15653 | 4/1998 |
| WO | WO 98/40517 | 9/1998 |
| WO | WO 98/54359 | 12/1998 |

OTHER PUBLICATIONS

Ahmed, et al.; "Major Historicompatibility Complex Susceptibility Genes for Dermatitis Herpetiformis Compared with Those for Gluten–sensitive Enterophaty", J. Exp. Med. 178: 2067–2075 (Dec. 1993).

Blakemore et al.; "Interleukin –1 Receptor Antogonist Gene Polymorphism as a Disease Severity Factor in Systemic Lupus Erythematosus", Arthritis & Rheumatism 37 (9): 1380–1385 (Sep. 1994).

Cabrera et al.; "Polymorphism in Tumor Necrosis Factor Genes Associated with Mucocutaneous Leishmaniasis", J. Exp. Med. 182: 1259–1264 (Nov. 1995).

Clay et al.; "Interleukin–1 Receptor Antagonist Gene Polymorphism Association with Lichen Sclerosus", Hum. Genet 94:–407–410 (1994).

Collins et al.; "Experimental Periodontitis Retards Hamster Fetal Growth", Journal of Dental Research, 74: p. 158 (Abstract No. 1171).

Collins et al.; "Effects of *Escherichia coli* and Porphyromonas Gingivalis Lipopolysaccharide on Pregnancy Outcome in the Golden Hamster", Infection and Immunity, 62 (1): 4652–4655 (Oct. 1994).

Collins et al.; "Effects of Porphyromonas Gingivalis Infection on Inflammatory Mediator Response and Pregnancy Outcome in Hamster", Infection and Immunity, 61 (10): 4356–4361 (Oct. 1994).

Dinarello A. Charles, "Interleukin–1 and Interleukin–1 Antagonism", Blood 77 (8): 1627–1652, (Apr. 15, 1991).

Dolan–Mullen et al.; "A Meta–analysis of Randomized Trials of Prenatal Smoking Cessation Interventions", Am. J. Obstet. Gynecol. 171: 1328–1334, (1994).

Eisenberg et al.; "Primary Structure and Functional Expression from Complementary DNA of a Human Interleukin–1 Receptor Antagonist", Nature 343: 341–346 (Jan. 25, 1990).

Emmons et al.; "Development of Wound Infections Among Women Undergoing Cesarean Section", Obstetrics & Gynecology, 72(4): 559–564 (Oct. 1988).

Ernest et al.; "Vaginal pH: A Marker of Preterm Premature Rupture of the Membranes", Obstetrics & Gynecology, 74(5): 734–737, (Nov. 1989).

(List continued on next page.)

Primary Examiner—Carla J. Myers
(74) Attorney, Agent, or Firm—Ivor R. Elriri, Esq.; Cynthia A. Kozakiewicz; Mintz, Levin, Cohn, Ferris, Glovsky and Popeo, P.C.

(57) ABSTRACT

Methods, assays and kits are disclosed for detecting a mother's or a fetus's susceptibility to an adverse pregnancy outcome such as low birth weight. The methods comprise obtaining a biological sample from a patient and determining the presence or absence of an IL-1 allele 2 of a marker that is associated with an adverse pregnancy outcome.

6 Claims, 3 Drawing Sheets

OTHER PUBLICATIONS

Figure 1:
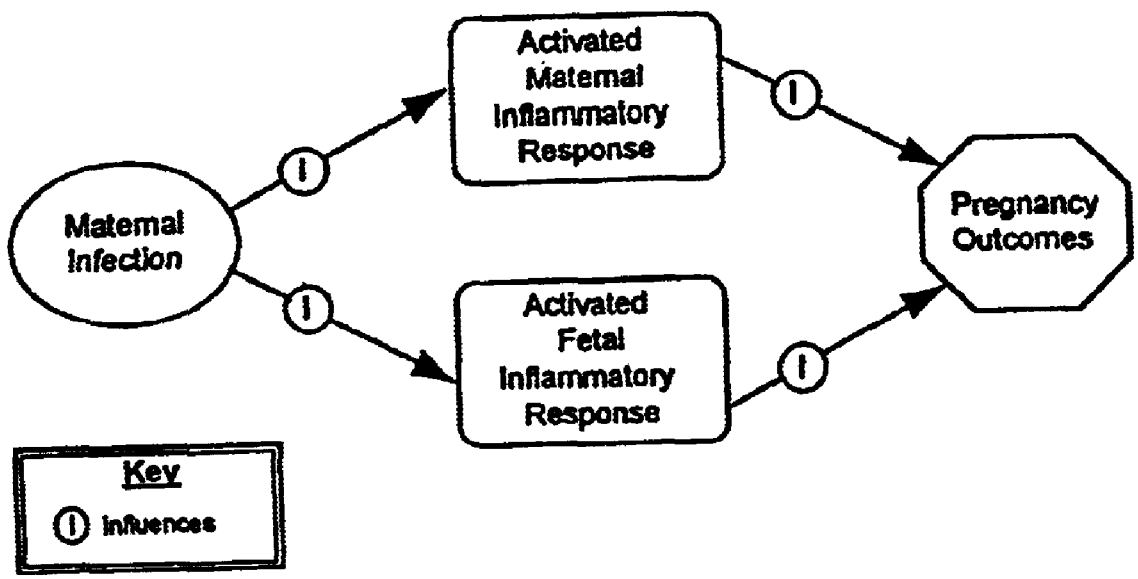

Gibbs et al.; "A Review of Premature Birth and Subclinical Infection", Am. J. Obstet. And Gynecol. 166 (5): 1515–1528 (May 1992).

Gratzner G. Howard,; "Monoclonal Antibody to 5–Bromo– and 5–Iododeoxyuridine: A New Reagent for Detection of DNA Replication", Science 218: 474–475 (Oct. 1982).

Gravett et al.; "Independent Associations of Bacterial Vaginosis and Chlamydia Trachomatis Infection with Adverse Pregnancy Outcome", JAMA, 256(14): 1899–1903 (Oct. 10, 1986).

Hillier et al.; "Association Between Bacterial Vaginosis and Preterm Delivery of a Low Birth–Weight Infant", The New England Journal of Medicine, 333(26): 1737–1742 (Dec. 28, 1995).

Hillier et al.,"A Case –Control Study of Chorioamnionic Infection and Histologic Chorioamnionitis In Prematurity", The New England Journal of Medicine, 319(15): 972–978 (Oct. 13, 1988).

Jacob O. Chaim; "Tumor Necrosis Factor α in Autoimmunity : Pretty Girl or Old Witch?", Immunology Today 13 (4): 122–125 (1992).

Kaiser Jocelyn; "Med School Receive Hughes Windfall", Science 271: 138–140 (Jan. 12, 1996).

Kent et al.; "The Effects of Interleukins 1 α and 1β on Prostaglandin Production by Cultured Human Fetal Membranes", Prostaglandins 46: 51–59 (1993).

Lopez bernal; "Prostaglandins, Chorioamnionitis and Preterm Labour", British Journal of Obstetrics and Gynaecology, 94:1156–1158 (Dec. 1987).

Mansfield et al.; "Novel Genetic Association Between Ulcerative Colitis and the Anti–Inflammatory Cytokine Interleukin–1 Receptor Antagonist", Gastroenterology 106: 637–642 (1994).

Martius et al.; "Relationship of Vaginal Lactobacillus Species, Cervical Chlamydia Trachomatis, and Bacterial Vaginosis to Preterm Birth", Obstetrics & Gynecology , 71(1): 89–95 (Jan. 1988).

Mazor et al.; "Changes in Amniotic Fluid Concentrations of Protaglandins $E_2$ and $F_{2\alpha}$ In Women with Preterm Labor", Israel Journal of Medical Sciences, 26(8): 425–428 (Aug. 1990).

McDonald et al.; "Vaginal Infection and Preterm Labor", British Journal of Obstetrics and Gynaecology, 98: 427–435 (May 1991).

McDowell et al.; "A Genetic Association Between Juvenile Rheumatoid Arthritis and A Novel Interleukin–1α Polymorphism", Arthritis and Rheumatism 38(2): 221–228 (Feb. 1995).

McGregor et al.; "Antenatal Microbiologic and Maternal Risk Factor Associated with Prematurity", Am. J. Obst. Gynecol. , 163: 1465–1473, ( Nov. 1990 ).

Minkoff et al.; "Risk Factors for Prematurity and Premature Rupture of Membranes: A Prospective Study of the Vaginal Flora in Pregnancy", Am. J. Obstet. Gynecol. 150: 965–972 (1984 ).

MØl vig et al.; "Endotoxin–Stimulated Human Monocyte Secretion of Interleukin 1, Tumour Necrosis Factor Alpha, and Prostaglandin $E_2$ Shows Stable Interindividual Differences", Scand. J. Immunol. 27: 705–716 (1988).

Nicklin et al.; "A Physical Map of the Region Encompassing the Human Interleukin–1 α, Interleukin 1β, and Interleukin–1 Receptor Antagonist Genes", Genomics 19: 382–384 (1994).

Newton et al.; "A Clinical and Microbiologic Analysis of Risk Factors for Puerperal Endometritis", Obstetrics & Gynecology, 75: 402–406 (1990).

Offenbacher et al.; "Periodontal Infection as a Possible Risk Factor for Preterm Low Birth Weight", J. Periodontol. 67(10 Suppl.): 1103–1113, (Oct. 1996).

Pociot et al.; "A TaqI Polymorphism in the Human Interleukin–1β (IL–1β) Gene Correlates with IL–1β Secretion in Vitro", European Journal of Clinical Investigation 296–402 (1992).

Parant M.; "Possible Mediators in Endotoxin–Induced Abortion", Research in Immunology , 141:164–168 (1990).

Pociot et al.; "Association of Tumor Necrosis Factor (TNF) and Class I I Major Histocompatibility Complex Alleles with the Secretion of TNF–α and TNF–β by Human Mononuclear Cells: a Possible Link to Insulin–dependent Diabetes Mellitus", Europ. J. Immunol. 23: 224–231 (1993 ).

Pociot et al.; "A TaqI Polymorphism in the Human Interleukin–1β ( I L–1β) Gene Correlates with I L– 1β Secretion in Vitro", European Journal of Clinical Investigation 22: 396–402 (1992).

Probert et al.; "The Type I Interleukin–I Receptor Acts in Series with Tumor Necrosis Factor (TNF) to Induce Arthritis in TNF–Transgenic Mice", European Journal of Immunology 25: 1794–1797, (1995).

Romero et al.; "Amniotic Fluid Prostaglandin $E_2$ In Preterm Labor", Prostaglandins Leukotrienes and Essential Fatty Acids, 34:141–145 (1988).

Romero et al.; "Interleukin–1 Stimulates Prostaglandin Biosynthesis by Human Amnion", Prostaglandins, 37(1): 13–22 (Jan. 1989).

Romero et al.; "Infection and Labor, III. Interleukin–1: A Signal for the Onset of Parturition", Am. J. Obstet. Gynecol. 160: 1117–1123, (1989).

Seckinger et al.; "A Urine Inhibitor of Interleukin 1 Activity Affects Both Interleukin 1α and 1β but not Tumor Necrosis Factor $α^{1}$", The Journal of Immunology , 139(5): 1541–1545, (Sep. 1, 1987).

Silver et al.; "Evidence Relating Bacterial Vaginosis to Intraamniotic Infection", Am. J. Obstet. Gynecol. 161: 808–812 (1989).

Smoak, W. Ida; "Embryopathic Effects of the Oral Hypoglycemic Agent Chlorpropamide in Cultured Mouse Embryos", Am. J. Obstet. Gynecol. 169: 409–414 , 1993).

Tamatani et al.; "Existence of Both IL–1α and β in Normal Human Amniotic Fluid: Unique High Molecular Weight Form of Il– 1β", Immunology 65: 337–342, (1988).

Tarlow et al.; "Severity of Alopecia Areata is Associated with a Polymorphism in the Interleukin–1 Receptor Antagonist Gene", J. Invest. Dermatol. 103: 387–390, (1994).

Vassali Pierre; "The Pathophysiology of Tumor Necrosis Factors", Ann. Rev. Immunol. 10: 411–452 , (1992).

Velden and Reitsma; "Amino Acid Dimorphism in I LI A is Detectable by PCR Amplification", Human Molecular Genetics, 2 (10): 1753, (1993).

Watts et al.; "Early Postpartum Endometritis: The Role of Bacteria, Genital Mycoplasmas, and Chlamydia Trachomatis", Obstetrics & Gynecology 73: 52–59 (1989).

Watts et al.; "Bacterial Vaginosis as a Risk Factor for Post–Cesarean Endometritis", Obstet. Gynecol. 75: 52–58, (1990).

Wilson et al.;"An Allelic Polymorphism within the Human Tumor Necrosis Factor α Promoter Region Is Strongly Associated with HLA A1, B8, and DR3 Allels", J. Exp. Med. 177: 557–560, (Feb. 1993).

Wilson et al.; "Genetics of Tumour Necrosis Factor–α in Autoi mmune, Infectious, and Neoplastic Disease", Journal of Inflammation 45: 1–12, (1995).

Offenbacher et al.; "Periodontal Infection as a Possible Risk Factor for Preterm Low Birth Weight", J. Periodontol. 67: 1103–1113, (1996).

International Search Report Completed on Mar. 28, 2000 and mailed on Jul. 04, 2000.

* cited by examiner

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 1
tgttctacca cctgaactag gc                                             22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 2
ttacatatga gccttccatg                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
tggcattgat ctggttcatc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
gtttaggaat cttcccactt                                              20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
ctcaggtgtc ctcgaagaaa tcaaa                                        25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
gcttttttgc tgtgagtccc g                                            21

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 7
atggttttag aaatcatcaa gcctagggca                                   30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
aatgaaagga ggggaggatg acagaaatgt                                   30

<210> SEQ ID NO 9
<211> LENGTH: 27
```

```
<212> TYPE: DNA
<213> ORGANISM: Artificial Sequence
<220> FEATURE:
<223> OTHER INFORMATION: Description of Artificial Sequence: Primer

<400> SEQUENCE: 9
ctatctgagg aacaaccaac tagtagc                                              27

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
taggacattg cacctagggt ttgt                                                 24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
aggcaatagg ttttgagggc cat                                                  23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
tcctccctgc tccgattccg                                                      20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 13
gaagcccctc ccagttctag ttc                                                  23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 14
cactccccat cctccctggt c                                                    21

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 15
```

-continued

```
ctcagcaaca ctccctat                                           17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 16
tcctggtctg caggtaa                                            17

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 17
aagcttgttc taccacctga actaggc                                 27

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 18
ttacatatga gccttccatg                                         20

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
tgtacctaag cccacccttt agagc                                   25

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
tggcctccag aaacctccaa                                         20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
gctgatattc tggtgggaaa                                         20

<210> SEQ ID NO 22
<211> LENGTH: 20
<212> TYPE: DNA
<213> ORGANISM: Artificial Sequence
```

-continued

```
<220> FEATURE:
<223> OTHER INFORMATION: Description of Artificial Sequence: Primer

<400> SEQUENCE: 22
ggcaagagca aaactctgtc                                                    20
```

FETAL TESTING FOR PREDICTION OF LOW BIRTH WEIGHT

RELATED APPLICATIONS

The present application is a continuation-in-part of International Application Number PCT/US99/08794, filed Apr. 21, 1999, which claims priority to U.S. Provisional Application No. 60/082,487, filed Apr. 21, 1998.

1 BACKGROUND OF THE INVENTION

1.1 Field of the Invention

The present invention relates to a genetic association between interleukins and low birth weight. Particularly, the invention relates to using fetal tissue to predict low birth weight delivery. The invention also provided kits for determination of susceptibility to low birth weight deliveries.

1.2 Brief Description of the Prior Art

In the United States there are about 250,000 spontaneous preterm births each year, occurring at less than 37 weeks gestation, resulting in birth weights under 2500 g or 5½ pounds. This obstetric problem accounts for about two-thirds of all neonatal mortality and over 5 billion dollars in ICU hospital costs each year. Furthermore, permanent disability among survivors is high, especially for respiratory and neurological disorders. Despite increased attention to maternal prenatal care over the last forty years and advances in medical care, most of the advances in infant mortality have been gained through improved capacity to improve the survival of the very low birth weight infants (i.e., those infants having a birth weight of <1500 g). Unfortunately, the incidence of spontaneous preterm births (SPB) has not significantly changed over the last decade. This has been attributed to the recognition that there is currently little understanding of the antecedent risk factors associated with spontaneous preterm births. Furthermore, there are currently no tests for identify mothers or fetuses at high risk. Recent data suggest that as much as 60% of the observed SPB has no suspected etiology. Maternal systemic infections and especially bacterial vaginosis have been shown to be an important source of preterm deliveries and histologic chorioamnionitis, which is highly correlated with SPB. However, other infectious or inflammatory processes may also be involved in SPB. Especially, since intraamniotic increases in $PGE_2$, IL-1 and TNF are consistently found in SPB, even in the absence of detectable infection.

Bacterial infections are associated with premature low birth weight (PLBW). Bacterial infections in the genitourinary tract have been reported to be a major risk factor for preterm delivery (1–4). In the largest study conducted to date by Hillier et al. (2) the relationship between bacterial vaginosis, preterm delivery and low birth weight was explored. In the study Hillier and her colleagues followed more than 10,000 women, from seven medical centers, from 23–26 weeks gestation through delivery. Vaginal cultures were taken to ascertain if bacterial vaginosis was present. Of the 10,397 women, 4.8% delivered PLBW infants. During this study it was also suggested that women who had urinary tract infections or used antibiotics prior to enrollment in the study were also more likely to deliver a PLBW infant. The data from this study demonstrated that 16% of the study population had bacterial vaginosis (BV) and that those 16% were 40% more likely to give birth prematurely than women without BV. The study also determined that bacterial vaginosis was associated with the preterm delivery of low birth weight infants independently of other recognized risk factors.

In other studies conducted by McGregor et al. (4) and Gravett et al. (5) it was postulated that the presence of bacterial vaginosis is associated with subclinical amniotic fluid infection in women with intact fetal membranes; an increased risk of abortion at less than 22 weeks; premature rupture of membranes (PROM), and preterm birth. Other studies have also shown the association between bacterial vaginosis and amniotic fluid infection, histological and clinical chorioamnionitis, placental infection, PROM, premature labor, preterm delivery and a higher maternal infectious morbidity postpartum (5–20). Thus, it appears likely that the genitourinary tract represents a major source of potential infectious challenge that contributes to PLBW.

Recently, a more distant chronic bacterial infection in the oral cavity, periodontitis, has, in certain aspects, been associated with PLBW deliveries. Offenbacher et al. (21) conducted a case control study on 124 pregnant or post-partum women. PLBW cases were defined as a mother with a birth weight of less than 2500 grams and one or more of the following: gestational age <37 weeks, preterm labor (PTL), or preterm premature rupture of membranes (PPROM). Controls were all normal birth weight infants (NBW). Certain types of severe periodontal disease was associated with an increased risk of PLBW (adjusted odds ratio of 7) after controlling for known obstetric PLBW risk factors such as smoking, race, alcohol usage, age, nutrition and genitourinary tract infection.

The primary bacteria involved in the genitourinary and periodontal infections are Gram-negative and are known to release the endotoxin lipopolysaccharide (LPS) into the tissue environment. There is substantial evidence that LPS is associated with pregnancy complications in animals. Endotoxins from enteric bacteria are capable of inducing placental necrosis, spontaneous abortions, fetal organ damage, fetal death and malformations (22).

When challenged with *E. coli* LPS, Lanning et al. (23) found that the embryological development of the golden hamster was affected, resulting in malformations, spontaneous abortions and low fetal weight. These series of experiments clearly demonstrated that infections in pregnant animals could elicit many pregnancy complications including spontaneous abortion, preterm labor, low birth weight, fetal growth restriction and skeletal anomalies. These experiments also supported the hypothesis that the bacteria associated with bacterial vaginosis, pelvic inflammatory disease and other sexually transmitted diseases have the potential to induce alterations that become evident at the outcomes of pregnancy.

In addition, recent studies (24, 25) involving the bacteria that are involved in periodontitis further suggest that chronic, non-disseminating infections, including those at distant sites, may strongly influence fetal outcomes. Of critical importance to these early experiments was the demonstration that these low-grade infections with low numbers of oral pathogens were not of sufficient magnitude to induce maternal malaise or fever. There was, however, a measurable local increase in PGE and TNFα, as well as a 15–18% decrease in fetal weight (26). Furthermore, the magnitude of the $PGE_2$ and TNFα response was inversely related to the weight of the fetuses, mimicking the intraamniotic changes seen in humans with PLBW (26). LPS dosing experiments demonstrated that higher levels of LPS could induce fever and weight loss in pregnant animals and resulted in more severe pregnancy outcomes including spontaneous abortions and malformations. These more dramatic outcomes were not seen in the low challenge-oral infection models, but rather resulted in a consistent decrease in fetal weight, and previous sensitizations or exposures to these pathogens prior to pregnancy enhanced the severity of the fetal growth restriction when a secondary exposure occurred during pregnancy (24, 25).

Inflammatory mediators such as prostaglandin $E_2$ ($PGE_2$) and interleukin-1 (IL-1) are present not only in all immunoinflammatory processes, but also regulate the normal physiologic process of parturition, as well as pathologic prematurity. Amniotic fluid levels of $PGE_2$ rise steadily throughout pregnancy until a critical threshold level is reached to induce labor, cervical dilation and delivery.

The role of prostaglandins in regulating the normal physiology of pregnancy has been well documented. Gibbs et al. (27) summarized the evidence supporting the role of prostaglandins in human labor. Treatment with prostaglandin inhibitors delays the process of mid-trimester abortion and the onset of labor and can arrest preterm labor. Parturition at term is associated with elevated amniotic fluid and maternal plasma concentrations of prostaglandins.

The association between preterm labor and changes in amniotic fluid concentrations of $PGE_2$ and prostaglandin $F2\alpha$ ($PGF2\alpha$) was studied in 30 women by Mazor et al. (28). They demonstrated that women with preterm labor and intraamniotic infection had significantly higher amniotic fluid concentrations of $PGE_2$ and $PGF2\alpha$ than women with preterm labor but without infection. This may be explained by the fact that amnion from women with preterm labor and histologic chorioamnionitis produced more $PGE_2$ than amnion from women without placental inflammation (29). Romero and co-workers (30) observed elevated levels of $PGE_2$ as a consistent and reproducible fact of PLBW even in the absence of clinical or subclinical genitourinary tract infection and they postulated that the majority of PLBW deliveries are "probably caused by an infection of unknown origin."

Tamatani has shown that interleukin-1 beta (IL-1β) is present in normal amniotic fluid (31) and Flynn has demonstrated production of IL-1β by human placental macrophages (32). The small amount of IL-1β detected in the second trimester amniotic fluid has been shown to exhibit a threefold increase with the onset of labor (33). Kent et al. (34) in a study on the effects of IL-1β on prostaglandin production by cultured human fetal membranes, has demonstrated that IL-1β is a potent stimulator of the synthesis of prostaglandins by decidua and by amnion. IL-1 was the first cytokine implicated in the onset of labor in the presence of infection. IL-1 is produced in vitro by human decidua in response to bacterial products (35,36). In patients with preterm labor and bacteria in the amniotic cavity, amniotic fluid IL-1 bioactivity and concentrations are elevated (36). Placental necrosis and fetal resorption can be induced in rats by the injection of recombinant human IL-1β on day 12 of gestation (37). Romero et al. (36) have also demonstrated among patients with PROM and bacteria in the amniotic cavity, that amniotic fluid IL-1β bioactivity and concentration is elevated with labor compared to those without labor. IL-1β stimulates prostaglandin production by amnion and decidua in vitro (38).

The role of infection and inflammatory mediators in pregnant hamsters has also been examined (39). These animals were infected in the oral cavity with bacteria known to cause periodontitis. After periodontitis was established in the hamsters, a statistically significant elevation of intraamniotic fluid levels of both PGE, and TNFα was observed, providing direct evidence that infections throughout the body can result in a change in the fatal environment. It is possible that both PGE and TNFα are produced by the periodontium and appear in the systemic circulation to eventually cross the chorioamniotic barrier and finally appear in the fluid. However, it seems more likely that blood borne bacterial products, especially LPS, target the chorioamniotic plexus to trigger local PGE and TNFα synthesis. Irrespective of targeting mechanism, it is clear that experimental infections in animal model can provide sufficient challenge to elicit LBW.

Figure 2:
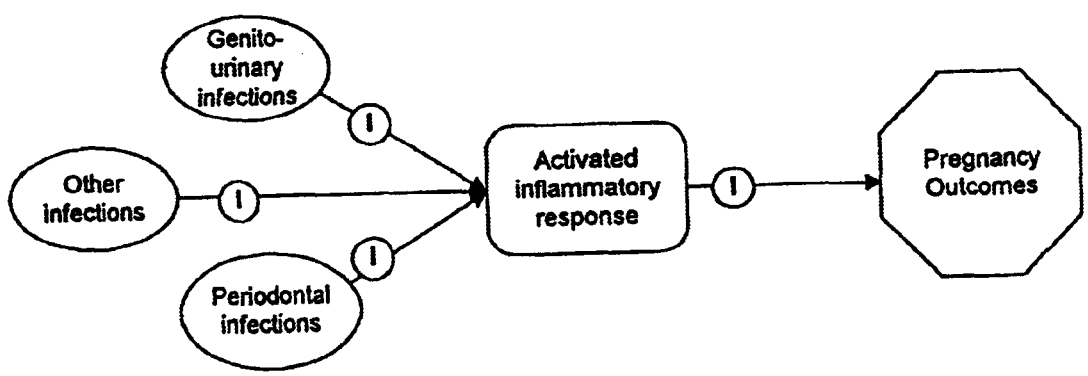

The data described above have led to the current clinical concept of the cause of PLBW outcomes, which may be described by the statements that are shown diagrammatically in FIGS. 1 and 2. Maternal infections activates the maternal inflammatory response which can then lead to an adverse pregnancy outcome (FIG. 2). Additionally, a maternal infection may activate the fetal inflammatory response, which in turn leads to an adverse pregnancy outcome (FIG. 1).

In the last few years, the more severe forms of several diseases were shown to be associated with genetic variations in the genes for the inflammatory cytokines IL-1α, IL-1β, IL-1 receptor antagonist (IL-1RA or IL-1RN), and TNFα. These findings, together with new insights about PLBW, has led to a new hypothesis of how infections and inflammatory mediators influence pregnancy outcomes. This is shown diagrammatically in FIG. 3.

The cytokines interleukin-1 (IL-1) and tumour necrosis factor (TNF) are important mediators of inflammatory responses, and appear to play a central role in the pathogenesis of many chronic inflammatory diseases (40, 41). It is now well that their biological activities in vivo are sufficient to reproduce local inflammation and matrix catabolism (42), by attracting and activating white blood cells to tissues, and stimulating their secretion of other lymphocytotropic cytokines and catabolic enzymes. Higher production of these cytokines have also been associated with response to infection, where local induction of IL-1 and TNF facilitates the elimination of the microbial invasion. Classic studies however also report that in some infectious conditions very high levels of monocytic cytokines are produced, which activate a cascade of concomitant events such as tissue catabolism, vascular reactivity and hyper-coagulation with damaging effects on the host (43, 44).

It has been demonstrated that there are stable interindividual differences in the rates of production of IL-1 and TNF (45), and the ability to produce higher or lower cytokine levels clusters in families (46). More recently, particular gene variants have been associated with stable differences in IL-1 protein production in vitro from monocytes (47, 48), or TNF rate of transcription in transfix B cells (49). From these and other data, it is clear that genetic factors are playing a role in the IL-1 and TNF systems, and that IL-1 and TNF themselves are reasonable candidate genes for susceptibility or severity of various diseases that involve IL-1, TNF, or the mediators that they activate.

In a normal situation, the extent and severity of inflammation is regulated by feedback mechanisms to a level sufficient to fight microbial invasion without long-lasting damage to the tissues involved. It can be speculated that dysregulated production of IL-1 and/or TNF in some individuals would over-ride the feedback mechanisms and lead to tissue damage, matrix catabolism, and the activation of various processes that respond to certain levels of these mediators.

The IL-1 family is composed of at least six proteins produced by three genes. IL-1α and IL-1β are produced as propeptides of 31–33 KDa that are cleaved at the cell-membrane to 17 KDa mature proteins (50). Of the precursor proteins, only pro-IL-1 is biologically active. IL-1 receptor antagonist (IL-1 RA or IL-1RN) (51, 52) is produced either as a secretory peptide with a leader sequence or as an intracellular form based on alternative first exons. Both IL-1 RA proteins bind to the IL-1 receptor but have no agonist activity. The IL-1A, IL-1B and IL1RN genes all lie within a 430 kb region on the long arm of human chromosome 2 (53).

Transcription of IL-1 is activated in human monocytes by bacterial agents and other cytokines (IL-1 itself; IFNγ; IL-2; TNFα). IL-1 agonists (IL-1α and IL-1β) induce transcription of inducible cyclooxygenase (COX-2), nitric oxide synthetase, collagenase and other matrix metalloproteinases, as well as many cytokines (such as IL-2, IL-4, IL-6, IL-8 and TNFα) (40). Down regulation of IL-1, up regulation of the IL-1 receptor, release of the soluble type II receptor, or predominance of IL-1RA, all limit the actions of IL-1, underlying the self-limitation of acute inflammation.

Similar biological actions are a consequence of tumour necrosis factor (TNF α or cachectin) or lymphotoxin (TNFβ or LTα) interaction with their receptor. TNFα is mainly produced by monocytes, and its biological functions are hard to separate from IL-1's (41). Both TNFα and LT proteins are, however, products of separate genes, which lie in the Class III region of Chromosome 6, not distant from the MHC complex (54).

The functional correlates of these gene variants include protein dimorphism for IL-1A(+4845) (Ser for Ala at 114) (55) and direct association with levels of IL-1β protein production in vitro for IL-1B(+3954). In the TNF cluster, at least five microsatellites and five single base variations have been described (TABLE 1), and TNF(+308) has been associated with 8-fold higher transcriptional activation rate in vitro (49).

TABLE 1

TNF Locus single-base polymorphisms

| Location | Ref |
|---|---|
| Exon IV, TNFB gene | (67) |
| Intron I, TNFB gene | (68) |
| Intron I, TNFB gene | (69) |
| −308, TNFA promoter | (70) |
| −238, TNFA promoter | (71) |

The early detection of a predisposition to genetic diseases presents the best opportunity for medical intervention in the progress of disease. Early prediction of risk may improve the prognosis for a patient through supervision and early intervention before the clinically detectable disorder occurs. In cases where patients with similar symptoms are treated with variable success, sophisticated genetic testing can differentiate individual patients with subtle or undetectable differences and can lead to more suitable individual treatments. Early intervention may involve methods such as gene therapy or treatment with drugs.

Genetic testing (also called genetic screening or genotyping) can be defined broadly as the testing of nucleic acid in an analytical capacity to determine if a patient has mutations (or alleles or polymorphisms) that either cause or increase susceptibility to a disease state or are in "linkage disequilibrium" with the gene causing a disease state.

With the development of genetic testing, it is now possible to identify gene mutations which indicate a propensity to develop disease, even when the disease is of polygenic origin. The number of diseases that can be identified by molecular biological methods continues to grow with increased understanding of the genetic basis of multifactorial disorders (see e.g., U.S. Pat. Nos. 4,582,788; 5,110,920; 4,801,531; 4,666,828; and 5,268,267). Genetic testing provides a means by which therapies can be targeted to those individuals in which they will be most effective depending upon the individuals genome type, a practice otherwise known as pharmacogenomics.

The IL-1 gene cluster is located on the long arm of chromosome 2 (2q13) and contains at least the genes for IL-1α(IL-1A), IL-1β(IL-1B), and the IL-1RN within a region of 430 Kb (Nicklin, et al., *Genomics* 19: 382–4 (1994)). The agonist molecules, IL-1α and IL-1β, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and the hepatic acute phase response. All three IL-1 proteins bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Inappropriate production of IL-1-axis components appears to play a central role in the pathology of many autoimmune and inflammatory diseases, including rheumatoid arthritis, inflammatory bowel disorder, psoriasis, and others. In addition, there are stable inter-individual differences in the rates of production of IL-1-axis components, and some of this variation may be accounted for by genetic differences at IL-1-axis gene loci (Molvig, et al., *Scand. J. Immunol.* 27:705–16 (1988); Pociot, et al., *Eur. J. Clin. Invest.* 22: 396–402 (1992)). Thus, the IL-1-axis genes are reasonable candidates for determining part of the genetic susceptibility to inflammatory diseases, most of which have a multifactorial etiology with a polygenic component.

Certain alleles from the IL-1 gene cluster are already known to be associated with particular disease states. For example, we have shown that IL-1RN allele 2 is associated with coronary artery disease (U.S. application Ser. No. 08/813,416), osteoporosis (U.S. Pat. No. 5,698,399, incorporated by reference herein), nephropathy in diabetes mellitus (Blakemore, et al., *Hum. Genet.* 97(3): 369–74 (1996)), alopecia areata (Cork, et al., *J. Invest. Dermatol.* 104(5 Supp.): 15S–16S (1995)), Graves disease (Blakemore, et al., *J. Clin. Endocrinol.* 80(1): 111–5 (1995)), systemic lupus erythematosus (Blakemore, et al., *Arthritis Rheum.* 37: 1380–85 (1994)), lichen sclerosis (Clay, et al., *Hum. Genet.* 94: 407–10 (1994)), and ulcerative colitis (Mansfield, et al., *Gastoenterol.* 106(3): 637–42 (1994)).

Likewise, the IL-1A allele 2 from marker −889 and IL-1B(TaqI) allele 2 from marker +3954 are associated with periodontal disease (U.S. Pat. No. 5,686,246, incorporated by reference herein). The IL-1A allele 2 from marker −889 is also associated with juvenile chronic arthritis, particularly chronic iridocyclitis (McDowell, et al., *Arthritis Rheum.* 38: 221–28 (1995)). The IL-1B(TaqI) allele 2 from marker +3954 of IL-1B is also associated with psoriasis and insulin dependent diabetes in DR3/4 patients (di Giovine, et al., *Cytokine* 7: 606 (1995); Pociot, et al., *Eur J. Clin. Invest.* 22: 396–402(1992)). Finally, the IL-1RN allele 1 is associated with diabetic retinopathy (GB Application No. 9618960.0).

Additionally, the following alleles from the IL-1 (33221461) haplotype are in linkage disequilibrium (GB Patent Application No. 9711040.7):

allele 3 of the 222/223 marker of IL-1A;
allele 3 of the gz5/gz6 marker of IL-1A;
allele 2 of the −889 marker of IL-1A;
allele 2 of the +3954 marker of IL-1B;
allele 1 of the −511 marker of IL-1B;
allele 4 of the gaat.p33330 marker;
allele 6 of the Y31 marker; and
allele 1 of the VNTR marker of IL-1RN.

Therefore, all of these alleles are associated to some degree with certain disease phenotypes.

However, although all of these alleles are in linkage disequilibrium with the actual disease-causing allele, none were previously believed to contribute to the disease state directly. Until now, no one has discovered an allele that produces a measurable phenotype which may actually contribute to the disease state.

The TNF locus in the class III region of the MHC is also a good candidate gene in autoimmune and inflammatory diseases, but because of the high degree of linkage disequilibrium across the MHC, it is difficult to determine which genes on a haplotype are important in the etiology of a disease. The haplotype HLA-A1-B8-DR3-DQ2, known as the autoimmune haplotype is associated with a number of autoimmune disease, including insulin dependent diabetes, Graves disease, myasthenia gravis, SLE, dermatitis herpetiformis and coeliac disease (61, 62, 63). A biallelic polymorphism at position −308 of the TNF promoter has been studied in these diseases, since it has been shown that (a) high TNF production levels have been associated with particular DR3 and DR4 haplotypes (46) and (b) that the TNF2 allele at −308 is carried on the autoimmune haplotype (64). However, in all the diseases mentioned above, it has not been possible to demonstrate any association of TNF with disease independently of the association with the autoimmune haplotype.

It seems that TNF does have an important role to play in infectious diseases; in a large study of patients with malaria in the Gambia, TNFα homozygosity was strongly associated with death from cerebral malaria, and no association with clinical outcome was found with any other marker in the class I and II regions of the MHC (65). Similar data have recently been reported in cutaneous leishmaniasis. (66).

During normal pregnancy, maternal hormones and locally-acting cytokines play a key role in regulating the onset of labor, cervical ripening, uterine contraction and delivery. Maternal infections during pregnancy have been demonstrated to perturb this normal cytokine and hormone regulated gestation, sometimes resulting in SPB. Recent findings have suggested that chronic infections that are not associated with the genitourinary tract may also contribute to SPB. Specifically, data suggest that a relatively common chronic oral infection, periodontitis, may provide sufficient challenge to the mother to trigger SPB. Data from pregnant animal models have demonstrated that low-grade, non-disseminating infections with *P. gingivalis* can result in diminished fetal growth. Furthermore, the magnitude of the fetal growth inhibition is inversely related to the maternal production of $PGE_2$ and TNFα, mimicking previous findings in humans. Experimental periodontitis in the pregnant hamster induced a 20% decrease in fetal weight (P=0.002). Periodontal infection is also associated with a significant rise in intra-amniotic $PGE_2$ from 3.31±1.1 ng/mL to 13.5±4.1 ng/mL at P=0.03 in the hamster. Three independent case-control studies in humans have been conducted examining the relationship between periodontal status and SPB, suggesting that the periodontal status is worse in SPB mothers, as compared to normal birth weight, full-term delivery (FT) controls. In the first study of 48 mothers, periodontal status was significantly worse in cases vs controls (mean attachment levels 3.25±0.05 mm vs 3.06±0.06 mm, P=0.02). In a recently reported case-control study of 124 pregnant mothers, periodontal disease status was significantly worse in SPB mothers compared to FT controls (P<0.005), controlling for a variety of well-established risk factors. Findings from this study suggest that among primiparous mothers, the odds of being in the SPB group was elevated more than 7 fold if more severe periodontal disease was present. This association was significant even adjusting for a variety of obstetric confounders and covariates by logistic regression analyses. These findings of an association between periodontal disease and SPB have been supplemented with new data from a second 48 case-control study which have added more sensitive measures of current periodontal disease status. Results indicate that gingival crevicular fluid PGE2 ($GCF-PGE_2$) levels are significantly higher in SPB mothers compared with FT controls [131.4±21.8 vs 62.6±10.3 (mean±SE, ng/mL), respectively at P=0.02]. Furthermore, within SPB mothers there was a significant inverse association between birth weight (as well as gestational age) and $GCF-PGE_2$ levels at P=0.023. These data suggest a dose-response relationship for increasing $GCF-PGE_2$, as a marker of current periodontal disease activity and decreasing birth weight. Furthermore, GCF-IL-1 levels were greatly elevated in SPB women, as compared to FT mothers, but the wide variance prevented statistical significance with this sample size [1217.8±281.3 ng/mL for SPB vs 720±105.2 ng/mL for FT]. In this third study the periodontal disease was more severe in PLBW mothers, as determined by biochemical and microbial biomarkers, but the difference in clinical attachment levels did not reach statistical significance (P=0.11).

2 SUMMARY OF THE INVENTION

In one aspect, the present invention provides novel methods for identifying whether a patient or a fetus is predisposed to an adverse pregnancy outcome such as premature preterm low birth weight delivery (LBW). In one embodiment, the method comprises determining whether an LBW associated allele is present in a nucleic acid sample obtained from the subject or the fetus. In a preferred embodiment, the LBW associated allele is IL-1A (+4845) allele 2 and/or an IL-1 (−511) allele 2, or alternatively a nucleic acid sequence that is in linkage disequilibrium with IL-1A (+4845) allele 2 and/or an IL-1 (−511) allele 2.

The LBW associated allele can be detected by any of a variety of techniques including: 1) performing a hybridization reaction between a nucleic acid sample and a probe that is capable of hybridizing to an LBW associated allele; 2) sequencing at least a portion of an LBW associated allele; or 3) determining the electrophoretic mobility of an LBW associated allele or fragment thereof (e g., fragments generated by endonuclease digestion). The allele can optionally be subjected to an amplification step prior to performance of the detection step. Preferred amplification steps are selected from the group consisting of: the polymerase chain reaction (PCR), the ligase chain reaction (LCR), stand displacement amplification (SDA), cloning, and variations of the above (e.g. RT-PCR and allele specific amplification). Primers for amplification may be selected to either flank the marker of interest (as required for PCR amplification) or directly overlap the marker (as in ASO hybridization). Oligonucleotides primers that hybridize to IL-1 and TNFA genes can easily be selected with commercially available primer selection programs. In a particularly preferred embodiment, the sample is hybridized with a set of primers, which hybridize 5' and/or 3' in a sense or antisense sequence to the ILD associated allele, and is subjected to a PCR amplification.

In another aspect, the invention features kits for performing the above-described assays. The kit can include nucleic acid sample collection means and a means for determining whether a subject carries an LBW associated allele. The kit may also comprise control samples, either negative or positive, or standards. The kit may also include an algorithmic device for assessing identity match. The algorithmic device may be used in conjunction with controls, or may be used independently of controls. The kits of the invention may also contain a variety of additional components such as a DNA amplification reagent, a polymerase, a nucleic acid purification reagent, a restriction enzyme, a restriction enzyme buffer, a nucleic acid sampling device, deoxynucleotides (dNTPs), and the like. Information obtained using the assays and kits described herein (alone or in conjunction with information on another genetic defect or environmental factor, which contributes to LBW) is useful for determining whether a pregnant, non-pregnant or non-symptomatic subject has or is likely to have a LBW baby, or more generally, a disease or condition that is caused by or contributed to by the allelic pattern detected. In addition, the information alone or in conjunction with information on another genetic defect contributing to LBW allows customization of thy for preventing the onset of symptoms associated with LBW, or for preventing the progression of the disease to end-stage, irreversible fibrosis. For example, this information can enable a clinician to: 1) more effectively prescribe a therapeutic that will address the molecular basis of LBW; and 2) better determine the appropriate dosage of a particular therapeutic for a particular subject.

In yet a further aspect, the invention features methods for treating or preventing the adverse pregnancy outcome of a low birth weight delivery in a subject, by administering to the subject, a pharmaceutically effective amount of an LBW therapeutic of the invention. In still another aspect, the invention provides in vitro and in vivo assays for screening test compounds to identify LBW therapeutics. In one embodiment, the screening assay comprises contacting a cell transfected with an LBW causative mutation that is operably linked to an appropriate promoter with a test compound and determining the level of expression of a protein in the cell in the presence and in the absence of the test compound. In a preferred embodiment, the LBW causative mutation results in decreased production of IL-1 receptor antagonist, and increased production of the IL-1 receptor antagonist or TNF-α in the presence of the test compound indicates that the compound is an agonist of IL-1 receptor antagonist or TNF-α activity. In another embodiment, the invention features transgenic non-human animals and their use in identifying antagonists of IL-1α, IL-1β or TNF-α activity or agonists of IL-1Ra activity.

Other features and advantages of the invention will be apparent from the following detailed description and claims.

3 BRIEF DESCRIPTION OF THE DRAWINGS

FIG. 1: Diagram showing the relationship between maternal infection and fetal inflammatory response and the risk of adverse pregnancy outcome.

FIG. 2: Diagram showing the relationship between maternal infection and the risk of adverse pregnancy outcome.

Figure 3:
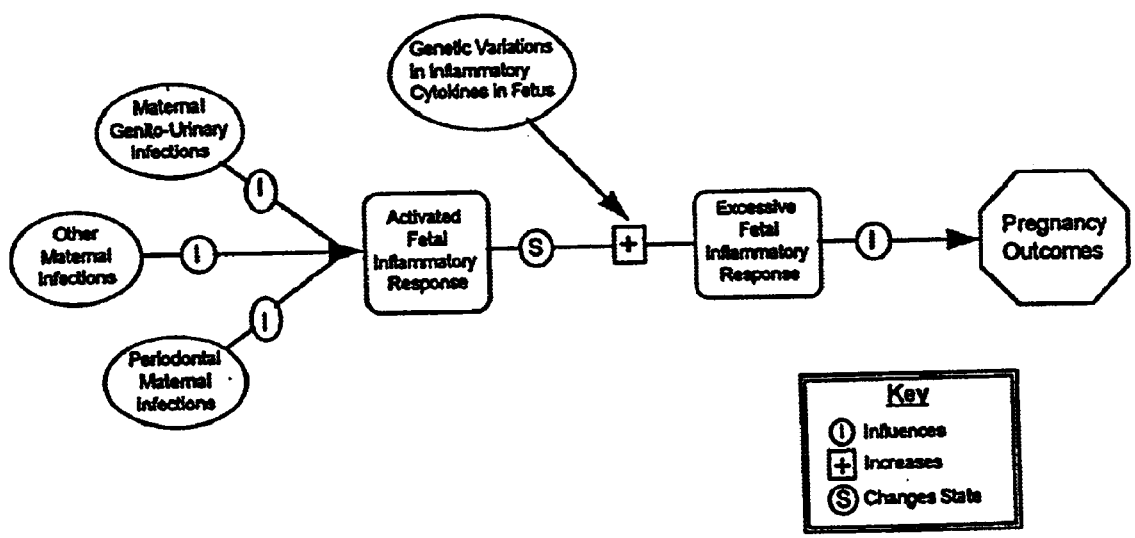

FIG. 3: Diagram showing the relationship between inflammatory cytokines and adverse pregnancy outcomes.

4 DETAILED DESCRIPTION

4.1 Abbreviations and Definitions

For convenience, the meaning of certain terms and phrases employed in the specification, examples and appended claims are provided below. In addition, these terms and phrases should be understood in relation to the specification as a whole.

The term "allele" refers to the different sequence variants found at different polymorphic sites in DNA obtained from a subject. For example, IL-1RN (VNTR) has at least five different alleles. The sequence variants may be single or multiple base changes, including without limitation insertions, deletions, or substitutions, or may be a variable number of sequence repeats. Allelic variants at a certain locus are commonly numbered in decreasing order of frequency. In a biallelic situation the frequent allele is allele 1, the rarer allele will be allele 2.

2/2—Refers to the homozygous allele 2/allele 2 state.

2/1—Refers to the heterozygous allele 2/allele 1 state.

The term "allelic pattern" refers to the identity of an allele or alleles at one or more polymorphic sites. For example, an allelic pattern may consist of a single allele at a polymorphic site, as for IL-1A (−889) allele 2, which is an allelic pattern having at least one copy of IL-1A allele 2 at position −889 of the IL-1A gene loci. Alternatively, an allelic pattern may consist of either a homozygous or heterozygous state at a single polymorphic site. For example, IL-1A (−889) allele 2,2 is an allelic pattern in which there are two copies of the second allele at the −889 marker of IL-1A and that corresponds to the homozygous IL-1A allele 2 state. Alternatively, an allelic pattern may consist of the identity of alleles at more than one polymorphic site.

"Allele detection"—Any means known to those skilled in the art of detecting or differentiating between alleles, e.g., detecting whether the allele at any given position of an IL gene is allele 1 or 2. We describe herein at least two means of determining which allele is present in a population. First, PCR amplification of the region followed by digestion of the PCR product and size fractionation. Second, PCR amplification of the region followed by detection with fluorescent labeled allele specific probes using the 5' exonuclease activity of the polymerase. However, numerous techniques for detecting a specific allele are known and need not be described herein.

The term "antibody" as used herein is intended to refer to a binding agent including a whole antibody or a binding fragment thereof which is specifically reactive with, e.g., an IL-1 or TNFα polypeptide. Antibodies can be fragmented using conventional techniques and the fragments screened for utility in the same manner as described above for whole antibodies. For example, F(ab)$_2$ fragments can be generated by treating an antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for, e.g, an IL-1 or TNFα polypeptide conferred by at least one CDR region of the antibody.

"Biological activity" or "bioactivity" or "activity" or "biological function", which are used interchangeably, for the purposes herein means an effector or antigenic function that is directly or indirectly performed by an IL-1 or TNFα polypeptide (whether in its native or denatured conformation), or by any subsequence thereof. Biological activities include binding to a target peptide, e.g., a receptor.

A bioactivity can be modulated by directly affecting the polypeptide. Alternatively, a bioactivity can be modulated by modulating the level of a polypeptide, such as by modulating expression of the gene encoding the polypeptide.

As used herein the term "bioactive fragment" refers to a fragment of a full-length polypeptide, wherein the fragment specifically mimics or antagonizes the activity of a wild-type polypeptide. The bioactive fragment preferably is a fragment capable of interacting with a receptor.

The term "an aberrant activity" refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but is still included within the scope of the term as used herein.

A "chimera," "mosaic," "chimeric mammal" and the like, refers to a transgenic animal, which has a knock-out or knock-in construct in at least some of its genome-containing cells.

The terms "control" or "control sample" refer to any sample appropriate to the detection technique employed The control sample may contain the products of the allele detection technique employed or the material to be tested. Further, the controls may be positive (e.g., IL-1A (−889) allele 2) or negative (e.g., allele 1, or the wild type, of the described marker) controls. By way of examples of end product controls, where the allele detection technique is PCR amplification, followed by size fractionation, the control sample may comprise DNA fragments of the appropriate size. Likewise, where the allele detection technique involves detection of a mutated protein, the control sample may comprise a sample of mutant protein. However, it is preferred that the control sample comprise the material to be tested. For example, the controls may be a sample of genomic DNA or a cloned portion of the IL-1 gene cluster. However, where the sample to be tested is genomic DNA, the control sample is preferably a highly purified sample of genomic DNA.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof. "Genotyping" refers to the analysis of an individual's genomic DNA (or a nucleic acid corresponding hereto) to identify a particular disease causing or contributing mutation or polymorphism, directly or based on detection of a mutation or polymorphism (a marker) that is in linkage disequilibrium with the disease causing or contributing gene.

The term "haplotype" refers to a set of alleles that are inherited together as a group (are in linkage disequilibrium).

As used herein, haplotype is defined to include those haplotypes that occur at statistically significant levels ($p_{corr} \leq 0.05$). As used herein, the phrase an "IL-1 haplotype" refers to a haplotype in the IL-1 loci and a "TNFA haplotype" refers to a haplotype in the TNFA loci.

The term "detecting alleles" refers to the process of genotyping, determining or identifying an allele or polymorphism. The allele actually detected might be a disease-causing mutation (e.g., allele 2), or a mutation that is in linkage disequilibrium with a disease-causing mutation. It will be manifest in the genomic DNA of a patient, but may also be detectable from RNA or protein sequences transcribed or translated from the region.

The term "hybridizes" refers to the annealing of one nucleic acid sequence to another. Appropriate stringency conditions which promote DNA hybridization, for example, 2 to 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. The salt concentration in the wash step can be selected from a low stringency of about 6.0×SSC to a high stringency of about 0.1×SSC. In addition, the temperature in the wash step can be increased from low stringency conditions at room temperature, about 22° C., to high stringency conditions at about 65° C. Formamide may be added to the hybridization steps and washing steps in order to decrease the temperature requirement by 1° C. per 1% formamide added.

A "low birth weight baby" is defined as baby having a birth weight of less than about 2500 grams and a gestational age of less than around 37 weeks (preterm) or preterm premature rupture of membranes. Likewise a "low birth weight mother" is a mother who has or is predisposed to giving birth to a low birth weight baby.

A "low birth weight associated allele" or "LBW associated allele" refers to an allele whose presence in a fetus or its mother indicates that the fetus or mother is susceptible to a low birth weight delivery. Examples of LBW associated alleles may include allele 2 of the +2018 marker of IL-1RN (contains an Msp I site); allele 2 of the −308 marker of TNFA (is not cut by Nco I), allele 2 of the VNTR marker of IL-1RN (240 bp PCR product); allele 4 of the 222/223 marker of IL-1A (132 mobility units (mu) PCR product); allele 4 of the gz5/gz6 marker of IL-1A (91 mu PCR product); allele 1 of the −889 marker of IL-1A (contains an NcoI site); allele 2 of the +4845 marker of IL-1A, allele 1 of the +3954 marker of IL-1B contains two TaqI sites); allele 2 of the −511 marker of IL-1B (contains a Bsu36I site); allele 3 of the gaat.p33330 marker (197 mu PCR product); and allele 3 of the Y31 marker (160 mu PCR product); allele 2 of the 1731 marker of the IL-1RN gene (A at position 1731); allele 2 of the 1812 marker of the IL-1RN gene (A at position 1812); allele 2 of the 1868 marker of the IL-1RN gene (G at position 1868); allele 2 of the 1887 marker of the IL-1RN gene (C at position 1887); allele 2 of the 8006 marker of the IL-1RN gene (contains an HpaII or MspI site), allele 2 of the 8061 marker of the IL-1RN gene (lacks an MwoI site) and allele 2 of the 9589 marker of the IL-1RN gene (contains an SspI site), and allele 2 TNF(−308).

An "LBW causative functional mutation" refers to a mutation which causes or contributes to the development of low birth weight delivery in a subject. Preferred mutations occur within the IL-1 complex or TNF-A. An LBW causative functional mutation occurring within an IL-1 gene (e.g. IL-1A, IL-1B or IL-1RN) a TNA A gene or a gene locus, which is linked thereto, may alter, for example, the open reading frame or splicing pattern of the gene, thereby resulting in the formation of an inactive or hypoactive gene product. For example, a mutation which occurs in intron 6 of the IL-1A locus corresponds to a variable number of tandem repeat 46 bp sequences corresponding to from five to 18 repeat units (Bailly, et al. (1993) *Eur. J. Immunol.* 23: 1240–45). These repeat sequences contain three potential binding sites for transcriptional factors: an SP1 site, a viral enhancer element, and a glucocorticoid-responsive element; therefore individuals carrying IL-1A intron 6 VNTR alleles with large numbers of repeat units may be subject to altered transcriptional regulation of the IL-1A gene and consequent perturbations of inflammatory cytokine production. Indeed, there is evidence that increased e number at this polymorphic IL-1A locus leads to decreased IL-1α synthesis (Bailly et al. (1996) *Mol Immunol.* 33: 999–1006). Alternatively, a mutation can result in a hyperactive gene product. For example, allele 2 of the IL-1B (C at +6912) polymorphism occurs in the 3' UTR (untranslated region) of the IL-1B mRNA and is associated with an approximately four-fold increase in the steady state levels of both IL-1B mRNA and IL-1B protein compared to those levels associated with allele 1 of the IL-1B gene (G at +6912). Further, an IL-1B (−511) mutation occurs near a promoter binding site for a negative glucocorticoid response element (Zhang et al. (1997) *DNA Cell Biol.* 16: 145–52). This element potentiates a four-fold repression of IL-1B expression by dexamethosone and a deletion of this negative response elements causes a 2.5-fold increase in IL-1B promoter activity. The IL-1B (−511) polymorphism may thus directly affect cytokine production and inflammatory responses. These examples demonstrate that genetic variants occurring in the IL-1A or IL-1B gene can directly lead to the altered production or regulation of IL-1 cytokine activity.

An "LBW therapeutic" refers to any agent or therapeutic regimen (including pharmaceuticals, nutraceuticals and surgical means) that prevents or postpones the development of or alleviates the symptoms of low birth weight in a subject. An LBW therapeutic can be a polypeptide, peptidomimetic, nucleic acid or other inorganic or organic molecule, preferably a "small molecule" including vitamins, minerals and other nutrients. Preferably an LBW therapeutic can modulate at least one activity of an IL-1 and/or TNF-α polypeptide, e.g., interaction with a receptor, by mimicking or potentiating (agonizing) or inhibiting (antagonizing) the effects of a naturally-occurring polypeptide. An agonist can be a wild-type protein or derivative thereof having at least one bioactivity of the wild-type, e.g., receptor binding activity. An agonist can also be a compound that upregulates expression of a gene or which increases at least one bioactivity of a protein. An agonist can also be a compound which increases the interaction of a polypeptide with another molecule, e.g., a receptor. An antagonist can be a compound which inhibits or decreases the interaction between a protein and another molecule, e.g., a receptor or an agent that blocks signal transduction or post-translation processing (e.g., IL-1 converting enzyme (ICE) inhibitors). Accordingly, a preferred antagonist is a compound which inhibits or decreases binding to a receptor and thereby blocks subsequent activation of the receptor. An antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind the active site of a protein and prevent it from interacting with target peptides. Yet other antagonists include antibodies interacting specifically with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site. An antagonist can be any class of molecule, including a nucleic acid, protein, carbohydrate, lipid or combination thereof, but for therapeutic purposes is preferably a small molecule. Preferred LBW therapeutics include: corticosteroids (e.g. prednisone and methylprednisone), cyclophosphamide (e.g. cytoxan), colchicine, azathioprine (e.g. Imuran), methotrexate, penicillamine, cyclosporine and other immunosuppressive agents (e.g. chlorambucil and vincristine sulfate).

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al. (1994) *Genomics* 19:382–84). The terms "IL-1A", "IL-1B", and "IL-1RN" as used herein refer to the genes coding for IL-1α, IL-1β, and IL-1 receptor antagonist, respectively. The gene accession number for IL-1A, IL-1B, and IL-1RN are X03833, X04500, and X64532, respectively.

"IL-1 functional mutation" refers to a mutation within the IL-1 gene cluster that results in an altered phenotype (i.e., effects the function of an IL-1 gene or protein). Examples include: IL-1A(+4845) allele 2, IL-1B (+3954) allele 2, IL-1B (+6912) allele 2 and IL-1RN (+2018) allele 2.

"IL-1X (Z) allele Y" refers to a particular allelic form, designated Y, occurring at an IL-1 locus polymorphic site in gene X wherein X is IL-1A, B, or RN or some other gene in the IL-1 gene loci, and positioned at or near nucleotide Z, wherein nucleotide Z is numbered relative to the major transcriptional start site, which is nucleotide +1, of the particular IL-1 gene X. As further used herein, the term "IL-1X allele (Z)" refers to all alleles of an IL-1 polymorphic site in gene X positioned at or near nucleotide Z. For example, the term "IL-1RN (+2018) allele" refers to alternative forms of the IL-1RN gene at marker +2018. "IL-1RN (+2018) allele 1" refers to a form of the IL-1RN gene which contains a cytosine (C) at position +2018 of the sense strand. Clay et al. (1996) *Hum. Genet.* 97:723–26. "IL-1RN (+2018) allele 2" refers to a form of the IL-1RN gene which contains a thymine (T) at position +2018 of the plus strand. When a subject has two identical IL-1RN alleles, the subject is said to be homozygous, or to have the homozygous state. When a subject has two different IL-1RN alleles, the subject is sad to be heterozygous, or to have the heterozygous state. The term "IL-1RN (+2018) allele 2,2" refers to the homozygous IL-1RN (+2018) allele 2 state. Conversely, the term "IL-1RN (+2018) allele 1,1" refers to the homozygous IL-1RN (+2018) allele 1 state. The term "IL-1RN (+2018) allele 1,2" refers to the heterozygous allele 1 and 2 state.

"IL-1 related" as used herein is meant to include all genes related to the human IL-1 locus genes on human chromosome 2 (2q 12–14). These include IL-1 genes of the human IL-1 gene cluster located at chromosome 2 (2q 13–14) which include: the IL-1A gene which encodes interleukin-1α, the IL-1B gene which encodes interleukin-1β, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1α, interleukin-1β, and interleukin-1RN are related in so much as they all bind to IL-1 type I receptors, however only interleukin-1α and interleukin-1β are agonist ligands which activate IL-1 type I receptors, while interleukin-1RN is a naturally occurring antagonist ligand.

Where the term "IL-1" is used in reference to a gene product or polypeptide, it is meant to refer to all gene products encoded by the interleukin-1 locus on human chromosome 2 (2q 12–14) and their corresponding homologs from other species or fictional variants thereof. The term IL-1 thus includes secreted polypeptides which promote an inflammatory response, such as IL-1α and IL-1β, as well as a secreted polypeptide which antagonize inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

An "IL-1 polypeptide" and "IL-1 protein" are intended to encompass polypeptides comprising the amino acid sequence encoded by IL-1 genomic DNA, and homologs thereof and include agonist and antagonist polypeptides.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "interact" as used herein is meant to include detectable relationships or associations (e.g., biochemical interactions) between molecules, such as interactions between protein-protein, protein-nucleic acid, nucleic acid-nucleic acid and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g., based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: IL-1A 5'/neo/IL-1A 3', where IL-1A 5' and IL-1A 3', refer to genomic or cDNA sequences which are, respectively, upstream and downstream relative to a portion of the IL-1A gene and where neo refers to a neomycin resistance gene. In another knock-out construct, a second selectable marker is added in a flanking position so that the gene can be represented as: IL-1A/neo/IL-1A/TK, where TK is a thymidine kinase gene which can be added to either the IL-1A5' or the IL-1A3' sequence of the preceding construct and which further can be selected against (i.e., is a negative selectable marker) in appropriate media. This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage equilibrium". The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are 100% in linkage disequilibrium with the two most frequent alleles of IL-1RN (VNTR), which are allele 1 and allele 2.

The term "marker" refers to a sequence in the genome that is known to vary among individuals. For example, the IL-1RN gene has a marker that consists of a variable number of tandem repeats (VNTR). The marker IL-1RN (+2018) as described herein can be used for identification of propensity to have a low birth weight delivery.

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

A "non-human animal" of the invention includes mammals such as rodents, non-human primates, sheep, dogs, cows, goats, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any members of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

The term "polymerase chain reaction" or "PCR" refers to a method of amplifying small amounts of DNA for ease of analysis. Many variations of the basic amplification protocol are well known to those of skill in the art. PCR based detection means include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long. Techniques for determining the presence of particular alleles would be those known to persons skilled in the art and include, but are not limited to nucleic acid techniques based on size or sequence, such as restriction fragment length polymorphism (RFLP), nucleic acid sequencing, or nucleic acid hybridization. The nucleic acid tested may be RNA or DNA. These techniques may also comprise the step of amplifying the nucleic acid before analysis. Amplification techniques are known to those of skill in the art and include, but are not limited to, cloning, polymerase chain reaction (PCR), polymerase chain reaction of specific alleles (PASA), polymerase chain ligation, nested polymerase chain reaction, and the like. Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

The term "propensity to disease," also "predisposition" or "susceptibility" to disease or any similar phrase, means that certain alleles are hereby discovered to be associated with or predictive of low birth weight delivery. The alleles are thus over-represented in frequency in individuals who delivered low birth weight babies as compared to healthy individuals. Thus, these alleles can be used to predict adverse pregnancy outcome even in pre-symptomatic individuals.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule to hybridize to at least approximately 6 consecutive nucleotides of a sample nucleic acid.

"Systemic rheumatologic disorder" refers to a disease selected from the group including at least the following disorders: systemic lupus erythematosis, Sjogren's syndrome, systemic sclerosis, dermatomyositis/polymyositis, mixed connective tissue disease, ankylosing spondylitis and the seronegative spondyloarthropathies.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgene" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the IL-1 or TNFα polypeptides, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques. The term is intended to include all progeny generations. Thus, the founder animal and all F1, F2, F3, and so on, progeny thereof are included.

The term "treating" as used herein is intended to encompass curing as well as ameliorating at least one symptom of a condition or disease.

The term "vector" refers to a nucleic acid molecule, which is capable of transporting another nucleic acid to which it has been linked. One type of preferred vector is an episome, i.e., a nucleic acid capable of extra-chromosomal replication Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.2 Fetal and Maternal Sampling

The present invention provides a method and kits for determining the risk of low birth weight delivery. Specifically, the method includes assessment of polymorphism patterns from fetal-derived or maternally-derived tissue. Suitable fetal-derived tissue includes, but is not limited to, fetal cells and/or cord blood. Methods for obtaining fetal cells are known to those skilled in the art, and include, but are not limited to amniocentesis, chorionic villus sampling, and harvesting nucleated fetal red blood cells present in maternal blood specimens. Suitable methods for obtaining fetal cells from maternal blood include, but are not limited to, those described in U.S. Pat. Nos. 5,629,147 and 5,457,024, incorporated by reference herein. In some cases, it may be useful to culture the fetal cells to provide a suitable volume for testing. The basis for testing fetal-derived tissue is based on recognition that the risk of low birth weight delivery is related to the polymorphism pattern of the fetal genome.

Fetal cells include, but are not limited to, fetal erythrocytes, lymphocytes and trophoblasts. Erythrocytes may also be in the form of undeveloped mature erythrocytes (although nucleated) such as, but not limited to, erythroblasts, normoblasts, and reticulocytes.

Approximately one in 4000 to one in 7000 erythrocytes in maternal blood are fetal erythrocytes. Fetal erythrocytes differ from maternal erythrocytes in that the fetal cells are nucleated, whereas maternal erythrocytes arc anuclear. Methods for detecting and isolating fetal cells from maternal blood include those described in Yeoh, S. C. et al. (1991) *Prenatal Diagnosis* 11:117–123; Mueller, U. W. et al. (1990) *Lancet* 336:197–200 (isolation of fetal trophoblasts by monoclonal antibodies); Price, J. O. et al. (1991) *Am. J. Obstet. Gynecol.* 165:1731–1737 (flow sorting); WO 91/07660 (antigen recognition); WO 91/16452; U.S. Pat. No. 5,153,117 (antibody binding); and U.S. Pat. No. 5,629,147 (intrinsic light scattering), all incorporated by reference herein.

Cells may be obtained from maternal peripheral blood, umbilical cord blood and chorionic villus sampling, for example. Cellular samples may be tested directly or the samples may be enriched, such as by cell culture. In an alternative embodiment, the tissue may be from embryonic cells fertilized in vitro or cells obtained by nuclear transfer techniques such as, but not limited to blastomere separation or nuclear transfer.

Provided in the present invention are kits for the predictions of adverse pregnancy outcomes. The kit includes reagents and probes needed to conduct the methods described herein. The kit may also contain one or more oligonucleotides capable of hybridizing near or at other alleles of the IL-1 gene cluster. PCR amplification oligonucleotides should hybridize between 25 and 2500 base pairs apart, preferably between about 100 and about 500 bases apart, in order to produce a PCR product of convenient size for subsequent analysis.

The oligonucleotides may be a variety of natural and synthetic compositions such as synthetic oligonucleotides, restriction fragments, cDNAs, synthetic PNAs, and the like. The kit may, optionally, also include DNA sampling means such as the AmpliCard™ (University of Sheffield, Sheffield, England S10 2JF; Tarlow J W, et al. (1994) *J. of Invest. Dermatol.* 103:387–389) and the like; DNA purification reagents such as Nucleon™ kits, lysis buffers, proteinase solutions and the like; PCR reagents, such as 10x reaction buffers, thermostable polymerase, dNTPs, and the like; and allele detection means such as the Hinf I restriction enzyme, allele specific oligonucleotides, and the like. Examples of labels which may be employed include radio-labels, enzymes, fluorescent compounds, streptavidin, avidin, biotin, magnetic moieties, metal binding moieties, antigen or antibody moieties, and the like.

4.3 Exemplary Polymorphisms and Oligonucleotides 4.3.1 IL-1B (−511) Gene Accession Number X04500

This C/T single base variation in the IL-1 beta promoter was described in 1990 (42). Oligonucleotide Primers:

5'-TGG.CAT.TGA-TCT.GGT.TCA.TC-3' (−702/−682) (SEQ ID No: 3)

5'-GTT.TAG.GAA.TCT.TCC.CAC.TT-3' (−417/−397) (SEQ ID No: 4)

$MgCl_2$ is used at 2.5 mM final, and PCR primers at 1 $\mu$M. cycling is performed at [95°, 1 min]×1; [95°, 1 min; 53°, 1 min; 72°, 1 min]×35; [72°, 5 min]×1; 4° C. Each PCR reaction is divided in two 25 $\mu$l aliquots: one is added of 3 Units of AvaI, the other 3.7 Units of Bsu 36I, in addition to 3 $\mu$l of the specific 10× restriction buffer. Incubation is at 37° C. overnight. Electrophoresis is by PAGE 9%. The two enzymes cut respectively the two different alleles. AvaI will produce 190+114 for allele 1, while it does not cut allele 2 (304 bp). Bsu 36I will produce 190+114 with allele 2, while allele 1 is uncut (304 bp). The restriction pattern obtained should be the inverse in the two aliquots (identifying homozygotes) or identical (heterozybotes). Frequencies in North British Caucasian population are 0.61 and 0.39. For 90% power at 0.05 level of significance in a similar genetic pool, 133 cases should be studied to detect 1.5 fold increase in frequency, or 505 for 0.1 absolute increase in frequency.

4.3.2 IL-1B (+3954) Gene Accession Number X04500

This polymorphism was described as TaqI RFLP of IL-1B (25). We have sequenced the most likely region implicated and found a C/T single base variation at +3954 in Exon V which fully explains the RFLP. We have designed PCR primers to insert a control TaqI site, hence the product will contain one constant and one polymorphic restriction site for TaqI. Oligonucleotide primers:

5'-CTC.AGG.TGT.CCT.CGA.AGA.AAT.CAA.A-3' (+3844/+3868) (SEQ ID No: 5)

5'-GCT.TTT.TTG.CTG.TGA.GTC.CCG-3' (+4017/+4037) (SEQ ID No: 6)

$MgCl_2$ is used at 2.5 mM final, and DNA template at 150 ng/50 $\mu$l PCR. Cycling is performed at [95°, 2 min]×1; [95°, 1 min; 67.5°, 1 min; 72° 1 min]×35; [72° 5 min]×1; 4° C. Each PCR reaction is added of 10 Units of TaqI (Promega) in addition to 3 $\mu$l of the specific 10× restriction buffer. Incubation is at 65° C. overnight. Electrophoresis is by PAGE 9%. The enzyme cuts a constant band of 12 bp (the absence of which indicates incomplete digestion) and either two further bands of 85 and 97 bp (allele 1), or a single band of 182 bp (allele 2). Frequencies in North British Caucasian population are 0.82 and 0.18. For 90% power at 0.05 level of significance in a similar genetic pool, 408 cases should be studied to detect 1.5 fold increase in frequency, or 333 for 0.1 absolute increase in frequency.

4.3.3 IL-1A (+4845) Gene Accession Number X03833

This single base variation (C/T) in Exon V was described by Gubler et al. in the cloning of human IL-1α (40) and reported again in a recent paper (41). We have designed new PCR primers to create an Fnu 4H1 restriction site in Allele 1 (A. G. Chaudhary, unpublished). Oligonucleotide Primers:

5'-ATG.GTT.TTA.GAA.ATC.ATC.AAG.CCT.AGG.GCA-3' (+4814/+4843) (SEQ ID No: 7)

5'-AAT.GAA.AGG.AGG.GGA.GGA.TGA.CAG.AAA.TGT-3b (+5015/+5044) (SEQ ID No: 8)

$MgCl_2$ is used at 1 mM final, and PCR primers at 0.8 $\mu$M. DMSO is added at 5% and DNA template at 150 ng/50 $\mu$l PCR. Cycling is performed at [95°, 1 min]×1; [94°, 1 min; 56°, 1 min; 72°, 2 min]×35; [72°, 5 min]×1; 4° C. Each PCR reaction is added of 2.5 Units of Fnu 4H1 (NEB) in addition to 2 $\mu$l of the specific 10× restriction buffer. Incubation is at 37° C. overnight Electrophoresis is by PAGE 9%. The enzyme Fnu 4H1 cuts a constant band of 76 bp (the absence of which indicates incomplete digestion) and two further bands of 29 and 124 bp with allele 1, or a single band of 153 bp for allele 2. Frequencies in North British Caucasian population are 0.71 and 0.29.

4.3.4 IL-1RN (+2018) Gene Accession Number X64532

This single base variation (C/T at +2016) in Exon 2 was described by Clay et al. (22). These primers (mismatched to the genomic sequence) were designed to engineer two enzyme cutting sites on the two alleles. The two alleles are 100% in linkage disequilibrium with the two most frequent alleles of IL-1RN (VNTR). Oligonucleotide Primers:

5'-CTA.TCT.GAG.GAA.CAA.CCA.ACT.AGT.AGC-3' (+1990/+2015) (SEQ ID No: 9)

5'-TAG.GAC.ATT.GCA.CCT.AGG.GTT.TGT-3' (+2133/+2156) (SEQ ID No: 10)

Cycling is performed at [96°, 1 min]×1, [94°, 1 min; 57°, 1 min; 70°, 2 min]×35; [7°, 5 min]×1, 4° C. Each PCR reaction is divided in two 25 $\mu$l aliquots: one is added of 5 Units of AluI, the other 5 Units of MspI, in addition to 3 $\mu$l of the specific 10× restriction buffer. Incubation is at 37° C. overnight. Electrophoresis is by PAGE 9%. The two enzymes cut respectively the two different alleles. AluI will produce 126+28 bp fragments for allele 1, while it does not digest allele 2 (154 bp). MspI will produce 125+29 bp with allele 2, while allele 1 is uncut (154 bp). Hence the two reactions (separated side by side in PAGE) will give inverted patterns of digestion for homozygote individuals, and identical patterns in heterozygotes. Allelic frequencies in a North British Caucasian population are 0.74 and 0.26. For 90% power at 0.05 level of significance in a similar genetic pool, 251 cases should be studied to detect 1.5 fold increase in frequency, or 420 for 0.1 absolute increase in frequency.

4.3.5 TNFA (−308) Gene Accession Number X02910

This single base variation (A/G) in the TNFA promoter was described by Wilson et al. in 1990 (43). One of the PCR primers has abase change to create an NcoI site when amplifying allele 1. Frequencies in North English White Caucasian population are 0.77 and 0.23. Oligonucleotide Primers:

5'-AGG.CAA.TAG.GTT.TTG.AGG.GCC-AT-3' (−331/−309) (SEQ ID No: 11)

5'-TCC.TCC.CTG.CTC.CGA.TTC.CG-3' (−244/−226) (SEQ ID No: 12)

$MgCl_2$ is used at 1.5, mM final, and PCR primers at 0.2 $\mu$M. Cycling is performed at [95°, 1 min]×1; [94°, 1 min; 60°, 1 min; 72°, 1 min]×35; [72°, 5 min]×1; 4° C. Each PCR reaction is added of 6 Units of NcoI in addition to 3 $\mu$l of the specific 10× restriction buffer. Incubation is at 37° C. overnight. Electrophoresis is by PAGE 6%. NcoI digestion will produce fragments of 87+20 bp for allele 1, while it does not cut allele 2 (107 bp). Heterozygotes will have the three bands. An alternative method of screening that was used in the original paper by Wilson et al. (32) uses single stranded conformation polymorphism (SSCP) analysis. For 90% power at 0.05 level of significance in a similar genetic pool, 297 cases should be studied to detect 1.5 fold increase in frequency, or 391 for 0.1 absolute increase in frequency.

4.3.6 TNFA (−238) Gene Accession Number X02910

This single base variation in the TNFA promoter was described by D'Alfonso et al. in 1993 (44). One of the PCR primers has a base change to create an AvaII site when amplifying allele 1. Oligonucleotide Primers:

5'-GAA.GCC.CCT.CCC.AGT.TCT.AGT.TC-3' (−425/−403) (SEQ ID No:13)

5'-CAC.TCC.CCA.TCC.TCC.CTG.GTC-3' (−236/−217) (SEQ ID No:14)

MgCl$_2$ is used at 2 mM final, and PCR primers at 0.25 μM. Cycling is performed at [94°, 3 min]×1; [94°, 1 min; 61°, 1 min; 72°, 1 min]×35; [72°, 5 min]×1; 4° C. Each PCR reaction is added of 5 Units of AvaII in addition to 3 μl of the specific 10× restriction buffer. Incubation is at 37° C. overnight. Electrophoresis is by PAGE 12%. AvaII will produce a constant band of 77 bp, the absence of which indicates incomplete digestion. In addition to this, allele 1 will be digested as 63+49+21 bp bands, allele 2 as 70+63 bp bands. Heterozygotes will have a mixed pattern of restriction. Frequencies in North English White Caucasian population are 0.94 and 0.06. For 90% power at 0.05 level of significance in a similar genetic pool, 1432 cases should be studied to detect 1.5 fold increase in frequency, or 149 for 0.1 absolute increase in frequency.

4.3.7 IL-1RN (VNTR) Gene Accession Number: X64532

The existence of a variable number of tandem repeats in intron 2 of IL-1RN gene was first reported during the cloning of the gene (38). This VNTR was characterized by Tarlow et al. (39) as a variable number (2 to 6) of 86 bp repeats. Oligonucleotide primers:

5' CTCAGCAACACTCCTAT 3' (+2879/+2895) (SEQ ID No: 15)

5' TCCTGGTCTGCAGGTAA 3' (+3274/+3290) (SEQ ID No: 16)

Cycling is performed at [96°, 1 min]×1; [94°, 1 min; 60°, 1 min; 72°, 2 min]×35; [70°, 5 min]×1; 4° C. Electrophoresis in 2% agarose, 90V, 30 min. The PCR product sizes are a direct indication of the number of repeats: the most frequent allele (allele 1) yields a 412 bp product. As the flanking regions extend for 66 bp, the remaining 344 bp imply four 86 bp repeats. Similarly, a 240 bp product indicates 2 repeats (allele 2), 326 is for 3 repeats (allele 3), 498 is 5 repeats 584 is 6 (allele 6). Frequencies in a North British Caucasian population for the four most frequent alleles are 0.734, 0.241, 0.021 and 0.004.

4.3.8. IL-1A (-889) Gene Accession Number X03833

The C/T single base variation in the IL-1A promoter was described by McDowell et al. (24). One of the PCR primers has a base change to create an NcoI site when amplifying allele 1 (cytosine at -889). Oligonucleotide Primers:

5'-AAG.CTT.GTT.CTA.CCA.CCT.GAA.CTA.GGC-3' (-967/-945) (SEQ ID No: 17)

5'-TTA.CAT.ATG.AGC.CTT.CCA.TG-3' (-888/-869) (SEQ ID No: 18)

MgCl$_2$ is used at 1 mM final, and PCR primers at 0.8 μM. Cycling is performed at [96°, 1 min]×1; [94°, 1 min; 50°, 1 min; 72°, 2 min]×45; [72°, 5 min]×1; 4° C. Each PCR reaction is added of 6 Units of NcoI in addition to 3 μl of the specific 10× restriction buffer. Incubation is at 37° C. overnight. Electrophoresis is by PAGE 6%. NcoI will produce 83+16 for allele 1, while it does not cut allele 2 (99 bp). Heterozygotes will have the three bands. Allelic frequencies in North English White Caucasian population are 0.71 and 0.29. For 90% power at 0.05 level of significance in a similar genetic pool, 214 cases should be studied to detect 1.5 fold increase in frequency, or 446 for 0.1 absolute increase in frequency.

4.4 Predictive Medicine 4.4.1 Polymorphisms Associated With LBW

The present invention is based, at least in part, on the identification of alleles that are associated (to a statistically significant extent) with the adverse pregnancy outcome of low birth weight or pre-mature low birth weight in subjects. In particular, as shown in the following examples, IL-1A (+4845) allele 2 and IL-1B (-511) allele 2 from the mother have been shown to be associated with LBW. Therefore detection of these alleles in a subject mother or her fetus indicate that the subject is predisposed to an adverse pregnancy outcome of a low birth weight baby. However, because these alleles are in linkage disequilibrium with other alleles, the detection of such other linked alleles can also indicate that the subject is predisposed to the development of LBW. For example, IL-1RN (+2018) allele 2, also referred to as exon 2 (8006) (GenBank: X64532 at 8006) polymorphism, Clay et al., Hum. Genet. 97:723–26, 1996, is in linkage disequilibrium with IL-1RN (VNTR) allele 2, which is a member of the 44112332 human haplotype. Cox et al., Am. J. Human Genet. 62:1180–88, 1998; International Patent Application No. PCT/GB98/01481. Further, the following alleles of the Il-1 (44112332) proinflammatory haplotype are known to be in linkage disequilibrium with IL-1RN (+2018): allele 4 of the 222/223 marker of IL-1A (a dinucleotide repeat polymorphism (HUGO GDB: 190869); allele 4 of the gz5/gz6 marker of IL-1A (a trinucleotide repeat polymorphism (HUGO GDB: 177384; Zuliani et al., Am. J. Hum. Genet. 46:963–69, 1990); allele 1 of the -889 marker of IL-1A (a single base variation marker—HUGO GDB: 210902; McDowell et al., Arthritis and Rheumatism 38:221–28, 1995); allele 1 of the +3954 marker of IL-1B (a single base C/T variation; di Giovine et al., Cytokine 7:606 (1995); Pociot et al. Eur J. Clin. Invest. 22:396–402, 1992); allele 2 of the -511 marker of IL-1B; allele 3 of the gaat.p33330 marker; and allele 3 of the Y31 marker.

Three other polymorphisms in an IL-1RN alternative exon (Exon 1ic, which produces an intracellular form of the gene product, GEN X77090) are in linkage disequilibrium with IL-1RN (+2018) allele 2. These include: the IL-1RN exon 1ic (1812) polymorphism (GenBank: X77090 at 1812); the IL-1RN exon 1ic (1868) polymorphism (GenBank: X77090 at 1868); and the IL-1RN exon 1ic (1887) polymorphism (GenBank: X77090 at 1887). Yet another polymorphism in the promoter for the alternatively spliced intracellular form of the gene, the Pic (1731) polymorphism (GenBank: X77090 at 1731), is also in linkage disequilibrium with IL-1RN (+2018) allele 2. The corresponding sequence alterations for each of these IL-1RN polymorphic loci is shown below.

| Allele No. | Exon 2 (+2018 of IL-1RN) | Exon 1ic-1 (1812 of GB: X77090) | Exon 1ic-2 (1868 of GB: X77090 | Exon 1ic-3 (1887 of GB:X77090) | Pic (1731 of GB: X77090) |
|---|---|---|---|---|---|
| 1 | T | G | A | G | G |
| 2 | C | A | G | C | A |

Clay et al., Hum. Genet. 97:723–26, 1996. For each of these polymorphic loci, the allele 2 sequence variant has been determined to be in linkage disequilibrium with IL-1RN (+2018) allele 2.

In addition to the allelic patterns described above, one of skill in the art can readily identify other alleles (including polymorphisms and mutations) that are in linkage disequilibrium with IL-1A (+4845) allele 2 or IL-1B (-511) allele 2, and are thereby associated with LBW. For example, a nucleic acid sample from a first group of subjects who have not had a low birth weight baby can be collected, as well as DNA from a second group of subjects who have had a low birth weight baby. The nucleic acid sample can then be compared to identify those alleles that are over-represented in the second group as compared with the first group, wherein such alleles are presumably associated with LBW.

Alternatively, alleles that are in linkage disequilibrium with an LBW associated allele can be identified, for example, by genotyping a large population and performing statistical analyses to determine which alleles appear more commonly together than expected. Preferably the group is chosen to be comprised of genetically related individuals. Genetically related individuals include individuals from the same race, the same ethnic group, or even the same family. As the degree of genetic relatedness between a control group and a test group increases, so does the predictive value of polymorphic alleles which are ever more distantly linked to a disease-causing allele. This is because less evolutionary time has passed to allow polymorphisms which are linked along a chromosome in a founder population to redistribute through genetic crossover events. Thus race-specific, ethnic-specific, and even family-specific diagnostic genotyping assays can be developed to allow for the detection of disease alleles which arose at ever more recent times in human evolution, e.g., after divergence of the major human races, after the separation of human populations into distinct ethnic groups, and even within the recent history of a particular family line.

Linkage disequilibrium between two polymorphic markers or between one polymorphic marker and a disease-causing mutation is a meta-stable state. Absent selective pressure or the sporadic linked reoccurrence of the underlying mutational events, the polymorphisms will eventually become disassociated by chromosomal recombination events and will thereby reach linkage equilibrium through the course of human evolution. Thus, the likelihood of finding a polymorphic allele in linkage disequilibrium with a disease or condition may increases with changes in at least two factors: decreasing physical distance between the polymorphic marker and the disease-causing mutation, and decreasing number of meiotic generations available for the dissociation of the linked pair. Consideration of the latter factor suggests that, the more closely related two individuals are, the more likely they will share a common parental chromosome or chromosomal region containing the linked polymorphisms and the less likely that this linked pair will have become unlinked through meiotic crossover events occurring each generation. As a result, the more closely related two individuals are, the more likely it is that widely spaced polymorphisms may be co-inherited. Thus, for individuals related by common race, ethnicity or family, the reliability of ever more distantly spaced polymorphic loci cm be relied upon as an indicator of inheritance of a linked disease or condition-causing mutation.

Appropriate probes may be designed to hybridize to a specific gene of the IL-1 locus, such as IL-1A, IL-1B or IL-1RN, TNFA or a related gene, the sequences of which are well known in the art. Alternatively, these probes may incorporate other regions of the relevant genomic locus, including intergenic sequences. Indeed the IL-1 region of human chromosome 2 spans some 400,000 base pairs and, assuming an average of one single nucleotide polymorphism every 1,000 base pairs, includes some 400 SNPs loci alone. Yet other polymorphisms available for use with the immediate invention are obtainable from various public sources. For example, the human genome database collects intragenic SNPs, is searchable by sequence and currently contains approximately 2,700 entries (http://hgbase.interactiva.de). Also available is a human polymorphism database maintained by the Massachusetts Institute of Technology (MIT SNP database (http://www.genome.wi.mit.edu/SNP/human/index.html)). From such sources SNPs as well as other human polymorphisms may be found.

For example, examination of the IL-1 region of the human genome in any one of these databases reveals that the IL-1 locus genes are flanked by a centromere proximal polymorphic marker designated microsatellite marker AFM220ze3 at 127.4 cM (centiMorgans) (see GenBank Acc. No. Z17008) and a distal polymorphic marker designated microsatellite anchor marker AFM087xa1 at 127.9 cM (see GenBank Acc. No. Z16545). These human polymorphic loci are both CA dinucleotide repeat microsatellite polymorphisms, and, as such, show a high degree of heterozygosity in human populations. For example, one allele of AFM220ze3 generates a 211 bp PCR amplification product with a 5' primer of the sequence TGTACCTAAGC-CCACCCTTTAGAGC (SEQ ID No: 19) and a 3' primer of the sequence TGGCCTCCAGAAACCTCCAA (SEQ ID No: 20). Furthermore, one allele of AFM087xa1 generates a 177 bp PCR amplification product with a 5' primer of the sequence GCTGATATTCTGGTGGGAAA (SEQ ID No:21) and a 3' primer of the sequence GGCAAGAG-CAAAACTCTGTC (SEQ ID No: 22). Equivalent primers corresponding to unique sequences occurring 5' and 3' to these human chromosome 2 CA dinucleotide repeat polymorphisms will be apparent to one of skill in the art. Reasonable equivalent primers include those which hybridize within about 1 kb of the designated primer, and which fiber are anywhere from about 17 bp to about 27 bp in length. A general guideline for designing primers for amplification of unique human chromosomal genomic sequences is that they possess a melting temperature of at least about 50° C., wherein an approximate melting temperature can be estimated using the formula $T_{melt}=[2\times(\# \text{ of A or T}) + 4\times(\# \text{ of G or C})]$.

A number of other human polymorphic loci occur between these two CA dinucleotide repeat polymorphisms and provide additional targets for determination of an LBW prognostic allele in a family or other group of genetically related individuals. For example, the National Center for Biotechnology Information web site (www.ncbi.nlm.nih.gov/genemap/) lists a number of polymorphism markers in the region of the IL-1 locus and provides guidance in designing appropriate primers for amplification and analysis of these markers.

Accordingly, the nucleotide segments of the invention may be used for their ability to selectively form duplex molecules with complementary stretches of human chromosome 2 q 12–13 or cDNAs from that region or to provide primers for amplification of DNA or cDNA from this region. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M–0.15M NaCl at temperatures of about 50° C. to about 70° C. Such selective conditions may tolerate little, if any, mismatch be the probe and the template or target strand.

4.2.2 Detection of Alleles

Many methods are available for detecting specific alleles at human polymorphic loci. The preferred method for detecting a specific polymorphic allele may depend, in part, upon the molecular nature of the polymorphism. For example, the preferred method of detection used for a single nucleotide polymorphism may differ from that employed for a VNTR polymorphism.

By way of general introduction, detection of specific alleles may be nucleic acid techniques based on hybridization, size, or sequence, such as restriction fragment length polymorphism (RFLP), nucleic acid sequencing, and allele specific oligonucleotide (ASO) hybridization. In one embodiment, the methods comprise detecting in a sample DNA obtained from a pregnant woman or her fetus the existence of an allele associated with LBW. For example, a nucleic acid composition comprising a nucleic acid probe including a region of nucleotide sequence which is capable of hybridizing to a sense or antisense sequence to an allele associated with LBW can be used as follows: the nucleic acid in a sample is rendered accessible for hybridization, the probe is contacted with the nucleic acid of the sample, and the hybridization of the probe to the sample nucleic acid is detected. Such technique can be used to detect alterations or allelic variants at either the genomic or mRNA level as well as to determine mRNA transcript levels, when appropriate.

A preferred detection method is ASO hybridization using probes overlapping an allele associated with LBW and has about 5, 10, 20, 25, or 30 nucleotides around the mutation or polymorphic region. In a preferred embodiment of the invention, several probes capable of hybridizing specifically to other allelic variants involved in LBW are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al., *Human Mutation* 7:244, 1996. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., *Proc. Natl. Acad. Sci. USA* 87:1874–78, 1990), transcriptional amplification system Kwoh, D. Y. et al., *Proc. Natl. Acad. Sci. USA* 86:1173–77, 1989), and Q-Beta Replicase (Lizardi, P. M. et al., *Bio/Technology* 6:1197, 1988).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to IL-1A (+4845) allele 2 or IL-1B (−511) allele 2 or any nucleic acid sequence in linkage disequilibrium with either of those alleles under conditions such that hybridization and amplification of the desired marker occurs, and (iv) identifying the amplification product. These detection schemes are especially useful for the detection of nucleic acid molecules if such molecules are present in very low numbers.

In a preferred embodiment of the subject assay, IL-1A (+4845) allele 2 or IL-1B (−511) allele 2 is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence IL-1A (+4845) allele 2 or IL-1B (−511) allele 2 or any nucleic acid sequence in linkage disequilibrium with either sequence. Exemplary sequencing reactions include those based on techniques developed by Maxim and Gilbert (*Proc. Natl. Acad. Sci. USA* 74:560, 1977) or Sanger (Sanger et al., *Proc. Nat. Acad. Sci. USA* 74:5463, 1977). It is also contemplated that any of a variety of automated sequencing procedures may be utilized when performing the subject assays (*Biotechniques* 19:448, 1995), including sequencing by mass spectrometry (see, for example PCT publication WO 94/16101; Cohen et al., *Adv. Chromatogr.* 36:127–62, 1996; and Griffin et al., *Appl. Biochem. Biotechnol.* 38:147–59, 1993). It will be evident to one skilled in the art that, for certain embodiments, the occurrence of only one, two or three of the nucleic acid bases need be determined in the sequencing reaction.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers et al., *Science* 230:1242, 1985). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. (See, for example, Cotton et al. (1988) *Proc. Natl. Acad. Sci. USA* 85:4397; Saleeba et al. (1992) *Methods Enzymol.* 217:286–95). In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al., *Carcinogenesis* 15:1657–62, 1994). According to an exemplary embodiment, a probe based on IL-1A (+4845) allele 2 or IL-1B (−511) allele 2 is hybridized to a cDNA or other DNA product from a test cell(s). The duplex is tied with a DNA mismatch repair enzyme, and the cleavage products, if any, can be detected from electrophoresis protocols or the like. (See, for example, U.S. Pat. No. 5,459,039.)

In other embodiments, alterations in electrophoretic mobility will be used to identify IL-1A (+4845) allele 2 or IL-1 B (−511) allele 2 or any nucleic acid sequence in linkage disequilibrium with either of them. For example, single strand conformation polymorphism (SSCP) may be used to detect differences in electrophoretic mobility between mutant and wild type nucleic acids (Orita et al., *Proc. Natl. Acad. Sci. USA* 86:2766, 1989, see also Cotton, *Mutat. Res.* 285:12544, 1993; and Hayashi, *Genet. Anal. Tech. Appl.* 9:73–79, 1992. Single-stranded DNA fragments of sample and control IL-1A (+4845) allele 2 or IL-1B (−511) allele 2 alleles or alleles of any nucleic acid sequence in linkage disequilibrium with either of them are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., *Trends Genet.* 7:5, 1991).

In yet another embodiment, the movement of IL-1A (+4845) allele 2 or IL-1B (−511) allele 2 alleles, or alleles of any nucleic acid sequence in linkage disequilibrium with those alleles in polyacrylamide gels containing a gradient of denaturant is assayed using denaturing gradient gel electrophoresis (DGGE) (Myers et al., *Nature* 313:495, 1985). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner, *Biophys. Chem.* 265:12753, 1987).

Examples of other techniques for detecting IL-1A(+4845) allele 2 or IL-1B (−511) allele 2 alleles or alleles of any nucleic acid sequence in linkage disequilibrium with them and other alleles associated with LBW include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al., *Nature* 324:163,1986); Saiki et al., *Proc. Natl. Acad. Sci. USA* 86:6230, 1989). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al., *Nucleic Acids Res.* 17:2437–2448, 1989) or at the extreme 3' end of one primer where, under appropriate conditions, mismatch can prevent, or reduce polymerase extension (Prossner, *Tibtech* 11:238, 1993. In addition it may be desirable to introduce a novel restriction site in the region of the mutation to create cleavage-based detection (Gasparini et al., *Mol. Cell Probes* 6:1, 1992). It is anticipated that in certain embodiments amplification may also be performed using Taq ligase for amplification (Barany, *Proc. Natl. Acad. Sci USA* 88:189, 1991). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren et al., *Science* 241:1077–80, 1988. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson et al., *Proc. Natl. Acad. Sci. USA* 87:8923–27, 1990. In this method, PCR is used to achieve the exponential amplification of target DNA, which is then detected using OLA.

Several techniques based on this OLA method have been developed and can be used to detect IL-1A (+4845) allele 2 or IL-1B (−511) allele 2 alleles or alleles of any nucleic acid sequence in linkage disequilibrium with them. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al., *Nucleic Acids Res.* 24:3728, 1996, OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Several methods have been developed to facilitate analysis of single nucleotide polymorphisms. In one embodiment, the single base polymorphism can be detected by using a specialized exonuclease-resistant nucleotide, as disclosed, e.g., in U.S. Pat. No. 4,656,127 (Mundy et al.). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. French Patent 2,650,840; PCT Appln. No. WO91/02087. As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet et al. in PCT Appln. No. 92/15712. The method of Goelet et al uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al., French Patent 2,650,840 and PCT Appln. No. WO91/02087, the method of Goelet et al. is preferably a heterogeneous phase assay, in which the primer or the target molecule is immobilized to a solid phase.

Recently, several primer-guided nucleotide incorporation procedures for assaying polymorphic sites in DNA have been described (Komher et al., *Nucleic Acids Res.* 17:7779–84, 1989; Sokolov, *Nucleic Acids Res.* 18:3671, 1990; Syvanen et al., *Genomics* 8:684–92, 1990; Kuppuswamy et al., *Proc. Natl. Acad. Sci. USA* 88:1143–47, 1991; Prezant et al., *Hum. Mutat.* 1:159–64, 1992; Ugozzoli et al., *GATA* 9:107–12, 1992; Nyren et al., *Anal. Biochem.* 208:171–75, 1993). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, et al., *Amer. J. Hum. Genet.* 52:46–59, 1993).

For mutations that produce premature termination of protein translation, the protein truncation test (PTT) offers an efficient diagnostic approach (Roest et. al., *Hum. Mol. Genet.* 2:1719–21, 1993; van der Luijt et. al., *Genomics* 20:1–4, 1994). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

In still another method known as Dynamic Allele Specific Hybridization (DASH), a target sequence is amplified by PCR in which one primer is biotinylated. The biotinylated product stand is bound to a streptavidin or avidin coated microtiter plate well, and the non-biotinylated strand is rinsed away with alkali. An oligonucleotide probe, specific for one allele, is hybridized to the target at low temperature. This forms a duplex DNA region that interacts with a double stand-specific intercalating dye. Upon excitation, the dye emits fluorescence proportional to the amount of double stranded DNA (probe-target duplex) present. The sample is then steadily heated while fluorescence is continually monitored. A rapid fall in fluorescence indicates the denaturing (or "Melting") temperature of the probe-target duplex. When performed under appropriate buffer and dye conditions, a single-base mismatch between the probe and the target results in a dramatic lowering of melting temperature (Tm) that can be easily detected (Howell, W. M. et al., (1999) Nature *Biotechnology* 17:)87–88.

Any cell type or tissue may be utilized in the diagnostics described herein. In a preferred embodiment the DNA sample is obtained from a bodily fluid, e.g., blood, obtained by known techniques (e.g., venipuncture) or saliva. Alternatively, nucleic acid tests can be performed on dry samples (e.g., hair or skin). When using RNA or protein, the cells or tissues that may be utilized must express the genes of the IL-1 loci.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, PCR in situ Hybridization Protocols and Applications (Raven Press, NY, 1992)).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Another embodiment of the invention is directed to kits for detecting a propensity for delivering a low birth weight baby. This kit may contain one or more oligonucleotides, including 5' and 3' oligonucleotides that hybridize 5' and 3' to an LBW associated marker (e.g., IL-1A (+4845) allele 2 and/or IL-1B (−511) allele 2), or any nucleic acid sequence in linkage disequilibrium with that marker, or detection oligonucleotides that hybridize to the LBW associated marker. The kit may also contain one or more oligonucleotides capable of hybridizing near or at other alleles of the TNFA gene or an IL-1 gene. PCR amplification primers should hybridize between 25 and 2500 base pairs apart, preferably between about 100 and about 500 bases apart, in order to produce a PCR product of convenient size for subsequent analysis.

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moities, metal binding moities, antigen or antibody moities, and the like.

The kit may, optionally, also include DNA sampling means such as the AmpliCard™ (University of Sheffield, Sheffield, England S10 2JF; Tarlow, et al., *J. of Invest. Dermatol.* 103:387–389, 1994) and the like; DNA purification reagents such as Nucleon™ kits, lysis buffers, proteinase solutions and the like; PCR reagents, such as 10× reaction buffers, thermostable polymerase, dNTPs, and the like; and allele detection means such as the HinfI restriction enzyme, allele specific oligonucleotides, degenerate oligonucleotide primers for nested PCR from dried blood.

4.4.3 Pharmacogenomics

Knowledge of the particular alleles associated with LBW delivery, alone or in conjunction with information on other genetic defects contributing to the same condition (the genetic profile of the particular condition or disease) allows a customization of the therapy for a particular condition or disease to the individual's genetic profile, the goal of "pharmacogenomics". For example, subjects having IL-1A (+4845) allele 2 and/or IL-1B (−511) allele 2 or any nucleic acid sequence in linkage disequilibrium with either allelic pattern may have or be predisposed to developing LBW and may respond better to particular therapeutics that address the particular molecular basis of the if disease in the subject. Thus, comparison of an individual's IL-1 and/or TNF-A profile to the population profile for the disease, permits the selection or design of drugs that are expected to be safe and efficacious for a particular patient or patient population (i.e., a group of patients having the same genetic alteration).

The ability to target populations expected to show the highest clinical benefit, based on genetic profile can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g., since measuring the effect of various doses of an agent on an LBW causative mutation is useful for optimizing effective dose).

The treatment of an individual with a particular therapeutic can be monitored by determining protein (e.g. IL-1α, IL-1β, IL-1Ra or TNAα), mRNA and/or transcriptional level. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level or amount of a protein, mRNA or genomic DNA in the preadministration sample; (iii) obtaining one or more post-administration samples from the subject; (iv) detecting the level of expression or activity of the protein, mRNA or genomic DNA in the post-administration sample; (v) comparing the level of expression or activity of the protein, mRNA or genomic DNA in the preadministration sample with the corresponding protein, mRNA or genomic DNA in the postadministration sample, respectively; and (vi) altering the administration of the agent to the subject accordingly.

Cells of a subject may also be obtained before and after administration of a therapeutic to detect the level of expression of genes other than an IL-1 gene or TNFα, to verify that the therapeutic does not increase or decease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

4.5 LBW Therapeutics

Modulators of IL-1 (e.g., IL-1α, IL-1β or IL-1 receptor antagonist) or TNFα or a protein encoded by a gene that is in linkage disequilibrium with an IL-1 or TNF-A gene can comprise any type of compound, including a protein, peptide, peptidomimetic, small molecule, or nucleic acid. Preferred agonists include nucleic acids (e.g., encoding an IL-1 protein or TNFα or a gene tat is up- or down-regulated by an IL-1 or TNFα protein), proteins (e.g. IL-1 or TNFα proteins or a protein that is up- or down-regulated thereby) or a small molecule (e.g., that regulates expression or binding of an IL-1 protein or TNFα). Preferred antagonists, which can be identified, for example, using the assays described herein, include nucleic acids (e.g., single (antisense) or double stranded (triplex) DNA or PNA and ribozymes), protein (e.g., antibodies) and small molecules that act to suppress or inhibit IL-1 or TNFA transcription and/or protein activity.

4.5.1 Effective Dose

Toxicity and therapeutic efficacy of such compounds can be determined by standard pharmaceutical procedures in cell cultures or experimental animals, e.g., for determining The $LD_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.2 Formulation and Use

Compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insulation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the compositions may take the form of for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g., endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gets, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention is further illustrated by the following examples which should not be construed as limiting in any way. The contents of all cited references (including literature references, issued patents, published patent applications as cited throughout this application) are hereby expressly incorporated by reference.

The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984); U.S. Pat. No. 4,683,195; U.S. Pat. No. 4,683,202; Nucleic Acid Hybridization (B. D. Hames & S. J. Higgins eds., 1984); U.S. Pat. No. 4,666,828; U.S. Pat. No. 5,192,659; U.S. Pat. No. 5,272,057; and U.S. Pat. No. 4,801,531.

4.6 Assays to Identify ILD Therapeutics

Based on the identification of mutations that cause or contribute to low birth weight delivery, the invention further features cell-based or cell free assays, e.g., for identifying LBW therapeutics. In one embodiment, a cell expressing an IL-1 receptor, TNFα receptor or a receptor for a protein that is encoded by a gene which is in linkage disequilibrium with TNF-A or an IL-1 gene, on the outer surface of its cellular membrane is incubated in the presence of a test compound alone or in the presence of a test compound and a IL-1, TNF-α or other protein and the interaction between the test compound and the receptor or between the protein (preferably a tagged protein) and the receptor is detected, e.g., by using a microphysiometer (McConnell et al. (1992) Science 257:1906). An interaction between the receptor and either the test compound or the protein is detected by the microphysiometer as a change in the acidification of the medium. This assay system thus provides a means of identifying molecular antagonists which, for example, function by interfering with protein-receptor interactions, as well as molecular agonist which, for example, function by activating a receptor.

Cellular or cell-free assays can also be used to identify compounds which modulate expression of an IL-1 or TNF-A gene or a gene in linkage disequilibrium therewith, modulate translation of an mRNA, or which modulate the stability of an mRNA or protein. Accordingly, in one embodiment, a cell which is capable of producing an IL-1, TNF-α or other protein is incubated with a test compound and the amount of protein produced in the cell medium is measured and compared to that produced from a cell which has not been contacted with the test compound. The specificity of the compound vis a vis the protein can be confirmed by various control analysis, e.g., measuring the expression of one or more control genes. In particular, this assay can be used to determine the efficacy of antisense, ribozyme and triplex compounds.

Cell-free assays can also be used to identify compounds which are capable of interacting with a protein, to thereby modify the activity of the protein. Such a compound can, e.g., modify the structure of a protein thereby effecting its ability to bind to a receptor. In a preferred embodiment, cell-free assays for identifying such compounds consist essentially in a reaction mixture containing a protein and a test compound or a library of test compounds in the presence or absence of a binding partner. A test compound can be, e.g., a derivative of a binding partner, e.g., a biologically inactive target peptide, or a small molecule.

Accordingly, one exemplary screening assay of the present invention includes the steps of contacting a protein or functional fragment thereof with a test compound or library of test compounds and detecting the formation of complexes. For detection purposes, the molecule can be labeled with a specific marker and the test compound or library of test compounds labeled with a different marker. Interaction of a test compound with a protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the protein or functional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an IL-1, TNF-α or other protein, (ii) an appropriate receptor, and (iii) a test compound; and (b) detecting interaction of the protein and receptor. A statistically significant change (potentiation or inhibition) in the interaction of the protein and receptor in the presence of the test compound, relative to the interaction in the absence of the test compound, indicates a potential antagonist (inhibitor). The compounds of this assay can be contacted simultaneously. Alternatively, a protein can first be contacted with a test compound for an appropriate amount of time, following which the receptor is added to the reaction mixture. The efficacy of the compound can be assessed by generating dose response curves from data obtained using various concentrations of the test compound. Moreover, a control assay can also be performed to provide a baseline for comparison.

Complex formation between a protein and receptor may be detected by a variety of techniques. Modulation of the formation of complexes can be quantitated using, for example, detectably labeled proteins such as radiolabeled, fluorescently labeled, or enzymatically labeled proteins or receptors, by immunoassay, or by chromatographic detection.

Typically, it will be desirable to immobilize either the protein or the receptor to facilitate separation of complexes from uncomplexed forms of one or both of the proteins, as well as to accommodate automation of the assay. Binding of protein and receptor can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the receptor, e.g. an $^{35}$S-labeled receptor, and the test compound, and the mixture incubated under conditions conducive to complex formation, e.g., at physiological conditions for salt and pH, though slightly more stringent conditions may be desired. Following incubation, the beads are washed to remove any unbound label, and the matrix immobilized and radiolabel determined directly (e.g., beads placed in scintilant), or in the supernatant after the complexes are subsequently dissociated. Alternatively, the complexes can be dissociated from the matrix, separated by SDS-PAGE, and the level of protein or receptor found in the bead fraction quantitated from the gel using standard electrophoretic techniques such as described in the appended examples. Other techniques for immobilizing proteins on matrices are also available for use in the subject assay. For instance, either protein or receptor can be immobilized utilizing conjugation of biotin and streptavidin.

Transgenic animals can also be made to identify agonists and antagonists or to confirm the safety and efficacy of a candidate therapeutic. Transgenic animals of the invention can include non-human animals containing an ILD causative mutation under the control of an appropriate endogenous promoter or under the control of a heterologous promoter.

The transgenic animals can also be animals containing a transgene, such as reporter gene, under the control of an appropriate promoter or fragment thereof. These animals are useful, e.g., for identifying drugs that modulate production of an IL-1 or TNF-α protein, such as by modulating gene expression. Methods for obtaining transgenic non-human animals are well known in the art. In preferred embodiments, the expression of the LBW causative mutation is restricted to specific subsets of cells, tissues or developmental stages utilizing, for example, cis-acting sequences that control expression in the desired pattern. In the present invention, such mosaic expression of a protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of a mutation can be regulated via site-specific genetic manipulation in vivo, are known to those skilled in the art.

The transgenic animals of the present invention all include within a plurality of their cells an LBW causative mutation transgene of the present invention, which transgene alters the phenotype of the "host cell". In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control e.g. tissue-specific, developmental stage-specific, inducible or repressible by externally added agents. This regulated control will result in genetic recombination of the target sequence only in cells where recombinase expression is mediated by the promoter element. Thus, the activation of expression of the LBW causative mutation transgene can be regulated via control of recombinase expression.

Use of the cre/loxP recombinase system to regulate expression of an LBW causative mutation transgene requires the construction of a transgenic animal containing transgenes encoding both the Cre recombinase and the subject protein. Animals containing both the Cre recombinase and the LBW causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal For review see Jaenisch, R. (1988) *Science* 240:1468–1474.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed, 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

5 EXEMPLIFICATION

5.1 Example 1

Genotype Analysis

Genotype analysis was performed using samples derived from maternal blood and characterized according to race. White women showed a trend towards association between individuals carrying at least 1 copy of allele 2 at +4845 and –511 and low birth weight with an odds ratio of 2.83 (95% CI 0.196–40.97). A significant association was demonstrated in black women carrying at least 1 copy of allele 2 of +4845 with an odds ratio of 4.8 (95% CI 1.155–19.951, P=0.033) with low birth weight. Furthermore, a significant association between low birthweight and genotype was demonstrated in black women carrying at least 1 copy allele 2 at each locus of +4845 plus –511 with and odds ratio of 8.89 (95% CI 1.934–40.855. P=0.0068).

5.2 Example 2

This is a prophetic example. In this experimental phase we will collect blood samples from 90 subjects for screening against a battery of potential gene candidate markers. Blood (7–12 mL), obtained during routine venipuncture will be collected in ACDC tubes and frozen at 80° C. Alternatively, fetal cells may be obtained as described herein above. As described above, methods for obtaining fetal cells are known to those skilled in the art, and include, but are not limited to amniocentesis, chorionic villus sampling, and harvesting nucleated fetal red blood cells present in maternal blood specimens. Suitable methods for obtaining fetal cells from maternal blood include, but are not limited to, those described in U.S. Pat. Nos. 5,629,147 and 5,457,024. Forty-five patients with a history of spontaneous preterm births will be chosen for study. The definitions we describe are those recently reviewed by Berkowitz and Papiemik (67). Low birth weight is usually defined as <2500 g. As stated previously we are primarily interested in low birth weight when it is associated with preterm premature rupture of membranes (preterm PROM) and preterm labor (PTL), as we have previously defined these terms. Intrauterine growth retardation is also of interest since it represents those cases with birth weights less than the 10th percentile for that gestational age. We will determine gestational ages by ultrasound as described by Hadlock (68). The cut-off weights for determining whether the infant has IUGR, i.e. below the 10th percentile we will use the chart adapted from Berkowitz. Note that corrections that are made for race, gender and parity. For example a white male born of a primiparous mother at 36 weeks would be considered IUGR if he weighed less than (2190+20+70+0) or 2280 grams. This would be at the extreme end of the low birth weight for this gestational age. This case definition refers to mothers with either preterm labor (<37 weeks gestation) or preterm premature rupture of membranes which results in a birth weight of less than 2200 g. In addition, blood will be collected from 45 mothers with normal, full-term deliveries and no history of previous obstetric complication. The exclusion criteria include hypertension, smoking, alcohol or drug abuse, diabetes, HIV, preclampsia, and multiple gestations for cases and controls.

Frozen blood will be thawed and DNA prepared using the QUIAmp DNA blood 96 spin isolation kit. DNA samples will be provided (2–10 ug DNA per sample) in coded vials. After the battery of genetic markers have been tested, the code will be broken to determine which polymorphisms are associated preferentially with SPB cases.

The specific polymorphisms that will be considered will include, but will not be limited to IL-1A (+4845), IL-1B (–511), IL-1B (+3954), IL-1RN (intron 2) VNTR and TNFA (–308) and TNFA (–238). If a specific candidate gene (or genes) is identified, this candidate gene will then be used for screening a larger population sample in example 2. If no candidate genes are identified, then a similar test will be performed on fetal cord blood to determine if there is a fetal genotype which confers risk. If the screening results are equivocal, then a decision will be made as to whether the sample size should be increased, or if cord and maternal blood should be assayed. It is expected, however, that one or more candidate genes will be identified as being associated with SPB. It is also possible that protective genotypes may be identified.

Given the relationship between periodontal disease and low birth weight, we expect that at least IL-1A allele 2 plus IL-1B (TaqI) allele 2 will be predictive of susceptibility to an adverse pregnancy outcome. Accordingly, U.S. Pat. No. 5,686,246 is incorporated by reference herein. Accordingly, provided herein is a method of predicting susceptibility to an adverse pregnancy outcome comprising determining a genetic polymorphism pattern in genomic DNA for IL-1A and IL-1B and comparing the pattern to a control sample, wherein the control sample comprises an IL-1A allele 2 and IL-1B (TaqI) allele 2, and wherein the similarity of the genetic polymorphism pattern to the control sample indicates susceptibility to an adverse pregnancy outcome. The step for identifying a genetic polymorphism pattern for IL-1A and/or IL-1B includes, but is not limited to, amplification of target DNA sequences using PCR, wherein the PCR primers are selected from the group consisting of:

5' TGT TCT ACC ACC TGA ACT AGG C 3' (SEQ ID No: 1);
5' TTA CAT ATG AGC CTT CCA TG 3' (SEQ ID No: 2);
5' TGG CAT TGA TCT GGT TCA TC 3' (SEQ ID No: 3);
5' GTT TAG GAA TCT TCC CAC TT 3' (SEQ ID No: 4);
5' CTC AGG TGT CCT CGA AGA AAT CAA A 3' (SEQ ID No: 5);
5' GCT TTT TTG CTG TGA GTC CCG 3' (SEQ ID No: 6).
5' ATGGTTTTAGAAATCATCAAGCCTAGGGCA 3' (SEQ ID No: 7)
5' AATGAAAGGAGGGGAGGATGACAGAAATGT 3' (SEQ ID No: 8)
5' CTATCTGAGGAACAACCAACTAGTAGC 3' (SEQ ID No: 9)
5' TAGGACATTGCACCTAGGGTTTGT 3' (SEQ ID No: 10)
5' AGGCAATAGGTTTTGAGGGCCAT 3' (SEQ ID No: 11)
5' TCCTCCCTGCTCCGATTCCG 3' (SEQ ID No: 12)
5' GAAGCCCCTCCCAGTTCTAGTTC 3' (SEQ ID No: 13)
5' CACTCCCCATCCTCCCTGGTC 3' (SEQ ID No: 14)
5' CTCAGCAACACTCCTAT 3' (SEQ ID No: 15)
5' TCCTGGTCTGCAGGTAA 3' (SEQ ID No: 16)
5' AAGCTTGTTCTACCACCTGAACTAGGC 3' (SEQ ID No: 17)
5' TTACATATGAGCCTTCCATG 3' (SEQ ID No: 18)

The IL-1B (−511) allele can be amplified using the primers designated in SEQ ID Nos: 3 and 4; the IL-1B (+3954) allele can be amplified using the primers designated in SEQ ID Nos: 5 and 6; the IL-1A (+4845) allele can be amplified using the primers designated in SEQ ID Nos: 7 and 8; the IL-1RN (+2018) allele can be amplified using the primer designed in SEQ ID Nos: 9 and 10; TNFA (−308) allele can be amplified using the primers designated in SEQ ID Nos: 11 and 12; the TNFA (−238) allele can be amplified using the primers designated in SEQ ID Nos: 13 and 14; the IL-1RN (VNTR) allele can be amplified using the primers designated in SEQ ID Nos: 15 and 16; the IL-1A (−889) allele can be amplified using the primers designated in SEQ ID Nos: 17 and 18.

5.3 Example 3

This is a prophetic example. Blood will be collected for genotyping from both pregnant mothers and fetal cord blood. About 400 cases will be available for genotyping and 800 full-term controls. The actual number of samples to be processed for genotyping will be determined based upon the results obtained from Example 1. The results will be incorporated into logistic risk models to determine the contribution of cytokine polymorphisms to SPB and to identify any possible interactions. It is anticipated that the specificity, sensitivity and predictive values of these genetic markers as predictors of SPB risk will be determined. Secondarily, the amniotic fluid will be analyzed for a small subset of cases and controls to determine the relationship between maternal/fetal genotypes and cytokine levels. Maternal GCF levels will also be available for $PGE_2$, IL-1 and TNF. By building multi-variate risk models incorporating traditional obstetric risk factors the potential for the genotype serving as a surrogate marker for another confounder or co-variate will be addressed. Finally, by determining the sensitivity, specificity and predictive values of this candidate genotype a new marker for SPB can be identified and validated.

REFERENCES

I. Gomez, R, Ghezzi, F., Romero, R., Munoz, H., Tolosa, J. E., and Rojas, I., 1995, Premature labor and intra-amniotic infection. Clinical aspects and role of the cytokines in diagnosis and pathophysiology, *Clin. Perinatol.* 22(2):281–342.

II. Hillier, S. L., Nugent, R. P., Eschenbach, D. A., Krohn, M. A., Gibbs, R. S., Martin, D. H., Cotch, M. F., Edelman, R., Pastorek, J. G., II, Rao, A. V. McNellis, D., Regan, J. A., Carey, J. C., and Klebanoff, M. A., 1995, Association between bacterial vaginosis and preterm delivery of a low-birthweight infant, The Vaginal Infections and Prematurity Study Group, *New Engl. J. Med.* 333:1737–1742.

III. Roush, W., 1996, Guarding against premature birth, *Science* 271:139–140.

IV. McGregor, J. A., French, J. L., Parker, R., Draper, D., Patterson, E., Jones, W., Thorsgard, K., and McFee, J., 1995, Prevention of premature birth by screening and treatment for common genital tract infections: results of a prospective controlled evaluation, *Am. J. Obstet. Gynecol.* 173(4):157–167.

V. Gravett, M. G., Nelson, H. P., DeRouen, T., Crutchlow, C., Eschenbach, J. A., and Holmes, K. K., 1986, Independent associations of bacterial vaginosis and *Chlamydia trachomatis* infection with adverse pregnancy outcome, *J. Am. Med. Assoc.* 256:1899–1903.

VI. McDonald, H. M., O'Loughlin, J. A., Jolley, P., Vigneswaran, P., and McDonald, P. J., 1991, Vaginal infections and preterm labor, *Brit. J. Obstet. Gynecol.* 98:427–435.

VII. Hillier, S. L., Martius, J., Krohn, M. J., Kiviat, N., Holmes, K. K., and Eschenbach, D. A., 1988, A case control study of chorioamnionic infection and chorioamnionitis in prematurity, *New Engl. J. Med.* 319:972–978.

VIII. Martius, J., and Roos, T., 1996, The role of urogenital tract infections in the etiology of preterm birth: a review, *Arch. Gynecol. Obstet.* 258:1–19.

IX. McGregor, J. A., French, J. L., Richter, R., Franco-Buff, A., Johanson, A., Hillier, S., Judson, F. N., and Todd, J. K., 1990, Antenatal microbiologic and maternal risk factor associated with prematurity, *Am. J. Obstet. Gynecol.* 163(5 Pt.1):1465–1473.

X. Watts, D. H., Eschenbach, D. A., and Kenny, G. E., 1989, Early postpartum endometritis: the role of bacteria, genital mycoplasmas and *Chlamydia trachomatis, Obstet. Gynecol.* 73:52–60.

XI. Watts, D. H., Krohn, M., Hillier, S. L., and Eschenbach, D. A., 1990, Bacterial vaginosis as a risk factor for post-cesarean endometritis, *Obstet. Gynecol.* 75:52–58.

XII. Eschenbach, D. A., Gravett, M. G., Chen, K. C. S, Hoyme, U. B., and Holmes, K. K., 1984, Bacterial vaginosis during pregnancy. An association with prematurity and postpartum complications, in: *Bacterial Vaginosis*, P. A. Mardh and D. Taylor-Robinson, eds., Almquist and Wiksell, Stockholm.

XIII. Petersen, E. E., Sanabria de Isele, T., Pelz, K., and Hillemans, H. G., 1985, Die Amniokolpitis, nicht nur ein aesthetisches Problem: erhöhtes Infektionsrisiko bei Geburt, *Geburtshilfe Frauenheilkd.* 45:43–47.

XIV. Minkoff, H., Grunebaum, A. N., Schwartz, R. H., Feldman, J., Cummings, M., Crombleholme, W., Clark, L., Pringle, G., and McCormick, W. M., 1984, Risk factors for prematurity and premature rupture of the membranes: a prospective study of the vaginal flora in pregnancy, *Am. J. Obstet. Gynecol.* 150:965–972.

XV. Fischbach, F., Kolben, M., Thurmayr, R., Hafter, R., Sedlaczek, E., Zieglmeier, M., Preisl, G., Weindler, J., and Graeff, H., 1988, Genitale Infektionen und Schwangerschaftsverlauf: eine prospektive Studie, *Geburtshilfe Frauenheilkd.* 48(7):469–478.

XVI. Martius, J., Krohn, M., Hillier, S. L., Stamm, W. E., Holmes, K. K., and Eschenbach, D. A., 1988, Relationships of vaginal *lactobacillus* species, cervical *Chlamydia trachomatis*, and bacterial vaginosis to preterm birth, *Obstet. Gynecol.* 71:89–95.

XVII. Emmons, S. L., Krohn, M., Jackson, M., and Eschenbach, D. A., 1988, Development of wound infections among women undergoing cesarean section, *Obstet. Gynecol.* 72:559–564.

XVIII. Ernest, J. M., Meis, P. J., Moore, M. L., and Swain, M., 1989, Vaginal pH: a marker of preterm premature rupture of the membranes, *Obstet. Gynecol.* 74:734–738.

XIX. Silver, H. M., Sperling, R. S., St.Clair, P. J., and Gibbs, R. S., 1989, Evidence relating bacterial vaginosis to intraamniotic infection, *Am. J. Obstet. Gynecol.* 161:808–812.

XX. Newton, E. R., Prihoda, T. J., and Gibbs, R. S., 1990, A clinical and microbiologic analysis of risk factors for puerperal endometritis, *Obstet. Gynecol.* 75:402–406.

XXI. Offenbacher, S., Katz, V., Fertik, G., Collins, J. G., Boyd, D., Maynor, G., McKaig, R., and Beck, J., 1996, Periodontal Infection as a risk factor for preterm low birth weight, *J. Periodontol.* 67:1103–1113.

XXII. Haesaert, B., and Omoy, A., 1986, Transplacental effects of endotoxemia on fetal mouse brain, bone and placental tissue, *Pedriatr. Pathol.* 5:167–181.

XXIII. Lanning, J. C., Hilbelink, D. R., and Chen, L. T., 1983, Teratogenic effects of endotoxin on the golden hamster, *Teratogenesis Carcinog. Mutag.* 3:145–149.

XXIV. Collins, J. G., Smith, M. A., Arnold, R. R., and Offenbacher, S., 1994, Effects of *Escherichia coli* and *Porphyromonas gingivalis* lipopolysaccharide on pregnancy outcome in the golden hamster, *Infect. Immun.* 62:10;4652–4655.

XXV. Collins, J. G., Windley, H. W. III, Arnold, R. R., and Offenbacher, S., 1994, Effects of a *Porphyromonas gingivalis* infection on inflammatory mediator response and pregnancy outcome in the hamster, *Infect. Immun.* 62:10;4356–4361.

XXVI. Dolan-Mullen, P., Ramirez, G., Groff, J. Y., 1994, A meta-analysis of randomized trials of prenatal smoking cessation interventions, *Am. J. Obstet. Gynecol.* 171:1328–1334.

XXVII. Gibbs, R. S., Romero, R., Hiller, S. L., Eschenbach, D. A., and Sweet, R. L., 1992, A review of premature birth and subclinical infection, *Am. J. Obstet. Gynecol.* 166:1515–28.

XXVIII. Mazor, M., Wiznitzer, A., Maymon, E., Leiberman, J. R., and Cohen, A., 1990, Changes in amniotic fluid concentrations of prostaglandins $E_2$ and $F_2$ in women with preterm labor, *Isr. J. Med. Sci.* 26:425–428.

XXIX. Bernal, A. L., Hansel, D. J., Soler, R. C., Kelling, J. W., and Turnbull, A. C., 1987, Prostaglandins, chorioamnionitis and preterm labor, *Brit. J. Obstet. Gynecol.* 94:1156–1158.

XXX. Romero, R., Wu, Y. K., Mazor, M., Hobbing, J. C., and Mitchell, M. D., 1988, Amniotic fluid prostaglandin $E_2$ in preterm labor, *Prostaglandins Leukot. Essent. Fatty Acids* 34:141–145.

XXXI. Tamatani, T., Tsunoda, H., Iwasaki, H., Kaneko, M., Hashimoto, T., and Onozaki, K., 1988, Existence of both IL-1a and IL-1b in normal amniotic fluid: unique high molecular weight form of IL-1, *Immunol.* 65:337–342.

XXXII. Flynn, A., Finke, J. H., and Hilfiker, M. L., 1982, Placental mononuclear phagocytes as a source of interleukin-1, *Science* 218:475–477.

XXXIII. Opsjøn, S., Wathen, N. C., Tingulstad, S., Wiedswang, G., Sundan, A., Waage, A., and Austgulen, R., 1993, Tumor necrosis factor, interleukin-1, and interleukin-6 in normal human pregnancy, *Am. J. Obstet. Gynecol.* 169:397–484.

XXXIV. Kent, A. S., Sun, M. Y., Sullivan, M. H., and Elder, M. G., 1993, The effects of interleukins 1 alpha and 1 beta on prostaglandin production by cultured human fetal membranes, *Prostaglandins* 46(1):51–59.

XXXV. Mitchell, M. D., Trautman, M. S., and Dudley, D. J., 1993, Cytokine networking in the placenta, *Placenta* 14:249–275.

XXXVI. Romero, R., Brody, D. T., Oyarzun, E., Mazor, M., Wu, Y. K., Hobbins, J. C., and Durum, S. K., 1989, Infection and labor. III. Interleukin-1: a signal for the onset of parturition, *Am. J. Obstet. Gynecol.* 160(5 Pt. 1):1117–1123.

XXXVII. Parant, M., 1990, Possible mediators in endotoxin-induced abortion, *Res. Immunol.* 141(2):164–168.

XXXVIII. Romero, R., Durum, S., Dinarello, C. A., Oyarzun E., Hobbins, J. C., and Mitchell, M. D., 1989, Interleukin-1 stimulates prostaglandin biosynthesis by human amnion, *Prostaglandin* 37(1):13–22.

XXXIX. Collins, J. G., Kirtland, B. C., Arnold, R. R., and Offenbacher, S., 1995, Experimental periodontitis retards fetal hamster growth, *J. Dent. Res.* 74(Spec. issue):158 (Abstr. 1171).

XL. di Giovine F S, Duff G W. Interleukin-1—the first Interleukin. Immunol Today 1990;1:13–20.

XLI. Beutler B, Cerami A. The biology of TNF-a primary mediator of the host response. Ann Rev Imm, 1989;7:625–655.

XLII. Probert L, Plows D, Kontogeorgos G, Kollias G. The type-i interleukin-1 receptor acts in series with tumor-necrosis-factor (TNF) to induce arthritis in tnf-transgenic mice. Eur J Immun 1995;25:1794–1797.

XLIII. Jacob CO. Tumor-necrosis-factor-alpha in autoimmunity—pretty girl or old witch. Immunol Today 1992;13:122–125.

XLIV. Vassalli P. The pathophysiology of tumor necrosis factors. Ann Rev Immunol 1992;10:411–452.

XLV. Mølvig J, Baek L, Christensen P, Manogue K R, Vlassara H, Platz P, Nielsen L S, Svejgaard A, Nerup J. Endotoxin-stimulated human monocyte secretion of interleukin-1, tumour necrosis factor alpha, and prostaglandin $E_2$ shows stable interindividual differences. Scand J Immunol 1988;27:705–716.

XLVI. Pociot F, Briant L, Jongeneel C V, Mølvig J, Worsaae H, Abbal M, Thomsen M, Nerup J, Cambon-Thomsen A. Association of tumor necrosis factor (TNF) and class II major histocompatibility complex alleles with the secretion of TNF- and TNF- by human mononuclear cells: a possible link to insulin-dependent diabetes mellitus. Eur J Immunol 1993;23:224–231.

XLVII. Pociot F, Mølvig J, Wogensen L, Worsaae H, Nerup J. A TaqI polymorphism in the human interleukin-1 (IL-1)

gene correlates with IL-1 secretion in vitro. Eur J Clin Invest 1992;22:396–402.

XLVIII. di Giovine F S, Cork M J, Crane A, Mee J B, Duff G W. Novel genetic association of an IL-1B gene variation at +3953 with IL-1 protein production and psoriasis. Cytokine 1995;7:606. (Abstract)

XLIX. Wilson A G, Symons J A, McDowell T L, McDevitt H O, Duff G W. Effects of a polymorphism in the human tumour necrosis factor alpha promoter on transcriptional activation. Proc Natl Acad Sci USA 1997; (in press).

L. Dinarello C A. Interleukin-1 and Interleukin-1 antagonism. Blood 1991;77:1627–1652.

LI. Seckinger P, Williamson K, Balavoine J F, Nach B, Mazzei G, Shaw A, Dayer J M. A urine inhibitor of interleukin-1 activity affects both IL-1 alpha and IL-1 beta but not TNF alpha. J Immunol 1987;139:1541–1545.

LII. Eisenberg S P, Evans R J, Arend W P, Verderber E, Brewer M T, Hannum C H, Thompson R C. Primary structure and functional expression from complementary DNA of a human interleukin-1 receptor antagonist. Nature 1990;343:341–346.

LIII. Nicklin M J H, Weith A, Duff G W. A physical map of the region encompassing the human interleukin-1, interleukin-1, and interleukin-1 receptor antagonist genes. Genomics 1994;19:382–384.

LIV. Wilson A G, di Giovine F S, Duff G W. Genetics of tumor necrosis factor alpha in autoimmune, infectious and neoplastic diseases. J Inflammation 1995;45:1–12.

LV. van den Velden P A, Reitsma P H. Amino-Acid dimorphism in IL-1A is detectable by PCR amplification. Hum Mol Genetics 1993;2:1753.

LVI. Blakemore A I F, Tarlow J K, Cork M J, Gordon C, Emery P, Duff G W. Interleukin-1 receptor antagonist gene polymorphism as a disease severity factor in systemic lupus erythematosus. Arthritis Rheum 1994;37:1380–1385.

LVII. Mansfield J C, Holden H, Tarlow J K, di Giovine F S, McDowell T L, Wilson A G, Holdsworth C D, Duff G W. Novel genetic association between ulcerative colitis and the anti-inflammatory cytokine interleukin-1 receptor antagonist. Gastroenterology 1994;106:637–642.

LVIII. Tarlow J K, Clay F E, Cork M J, Blakemore A I F, McDonagh A J G, Messenger A G, Duff G W. Severity of alopecia areata is associated with a polymorphism in the interleukin-1 receptor antagonist gene. J Invest Dermatol 1994;103:387–390.

LIX. Clay F E, Cork M J, Tarlow J K, Blakemore A I F, Harrington C I, Lewis F, Duff G W. Interleukin 1 receptor antagonist gene polymorphism association with lichen sclerosis. Hum Genet 1994;94:407–410.

LX. McDowell T L, Symons J A, Ploski R, Forre O, Duff G W. A genetic association between juvenile rheumatoid arthritis and a novel interleukin-1 polymorphism. Arthritis Rheum 1995;38:221–228.

LXI. Svejgaard A, Ryder L P. HLA and insulin-dependent diabetes—an overview. Genet Epidemiol 1989;6:1–14.

LXII. Welch T R, Beischel L S, Balakrishnan K, Quinlan M, West C D. Major histocompatibility complex extended haplotypes in systemic lupus-erythematosus. Dis Markers 1988;6:247–255.

LXIII. Ahmed A R, Yunis J J, Marcus-Bagley D, Yunis E J, Salazar M, Katz A J, Awdeh Z, Alper C A. Major histocompatibility complex susceptibility genes for dermatitis herpetiformis compared with those for gluten-sensitive enteropathy. J Exp Med 1993;178:2067–2075.

LXIV. Wilson A G, de Vries N, Pociot F, di Giovine F S, van der Putte L B A, Duff G W. An allelic polymorphism within the human tumor necrosis factor a promote region is strongly associated with HLA A1, B8, and DR3 alleles. J Exp Med 1993;177:557–560.

LXV. McGuire W, Hill V S, Allsopp C E M, Greenwood B M, Kwiatkowski D. Variation in the TNF-alpha promoter region associated with susceptibility to cerebral malaria. Nature 1994;371(6497):508–510.

LXVI. Cabrera M, Shaw M A, Sharples C, Williams H, Castes M, Convit J, Blackwell J M. Polymorphism in tumor-necrosis-factor genes associated with mucocutaneous leishmaniasis. J Exp Med 1995;182:1259–1264.

LXVII. Berkowitz, G. S. and Papiemik, 1993, Epidemiology of preterm birth, *Epidemiologic Reviews* 15(2):414–442.

LXVIII. Hadlock, F. P., 1994, Ultrasound determination of menstrual age, in: *Ultrasonography in Obstetrics and Gynecology*, p.86, Peter W. Callen, ed., 3rd Edition, W.B. Saunders Company.

What is claimed is:

1. A method for determining whether a female subject is predisposed to having a low birth weight baby, said method comprising the steps of:
   a) providing a nucleic acid sample from the subject; and
   b) detecting an IL-1A (+4845) allele 2 or an IL-1B (−511) allele 2, wherein detection of said allele indicates that the subject is predisposed to having a low birth weight baby.

2. The method of claim 1, wherein said detecting is selected from the group consisting of allele specific oligonucleotide hybridization; size analysis; sequencing; hybridization; 5' nuclease digestion; single-stranded conformation polymorphism; allele specific hybridization; primer specific extension; and oligonucleotide ligation assay.

3. The method of claim 1, wherein prior to the detecting step, the nucleic acid sample is subject to an amplification step.

4. The method of claim 2, wherein said size analysis is preceded by a digestion with a restriction enzyme.

5. A method of claim 4, wherein said restriction enzyme is selected from the group consisting of: NcoI, AluI and MspI.

6. The method of claim 1, wherein said subject is pregnant.

* * * * *